United States Patent
Mayer et al.

(10) Patent No.: US 10,912,818 B2
(45) Date of Patent: *Feb. 9, 2021

(54) USE OF MICROORGANISMS FOR THE PREVENTION AND TREATMENT OF INTESTINAL DISEASES

(71) Applicant: Ludwig Stocker Hofpfisterei GmbH, Munich (DE)

(72) Inventors: Jürgen Mayer, Munich (DE); Dirk Haller, Freising-Weihenstephan (DE); Anna Zhenchuk, Freising-Weihenstephan (DE); Thomas Hofmann, Freising-Weihenstephan (DE); Andreas Dunkel, Freising-Weihenstephan (DE); Michael Schemann, Freising-Weihenstephan (DE); Dagmar Krüger, Freising-Weihenstephan (DE)

(73) Assignee: Ludwig Stocker Hofpfisterei GmbH, Munich (DE)

( * ) Notice: Subject to any disclaimer, the term of this patent is extended or adjusted under 35 U.S.C. 154(b) by 315 days.

This patent is subject to a terminal disclaimer.

(21) Appl. No.: 15/669,412

(22) Filed: Aug. 4, 2017

(65) Prior Publication Data
US 2017/0333525 A1 Nov. 23, 2017

Related U.S. Application Data

(62) Division of application No. 14/765,682, filed as application No. PCT/EP2014/052129 on Feb. 14, 2014, now abandoned.

(30) Foreign Application Priority Data

Feb. 5, 2013 (EP) ..................... 13153996

(51) Int. Cl.
| | | |
|---|---|---|
| *C12P 13/00* | (2006.01) | |
| *C12N 1/00* | (2006.01) | |
| *A23L 33/135* | (2016.01) | |
| *A61K 38/17* | (2006.01) | |
| *A61K 35/747* | (2015.01) | |
| *C12R 1/225* | (2006.01) | |
| *C12R 1/24* | (2006.01) | |
| *C12R 1/25* | (2006.01) | |
| *C12N 1/26* | (2006.01) | |
| *A61K 35/00* | (2006.01) | |
| *A61K 38/00* | (2006.01) | |

(52) U.S. Cl.
CPC ........ *A61K 38/1787* (2013.01); *A23L 33/135* (2016.08); *A61K 35/747* (2013.01); *C12N 1/26* (2013.01); *C12P 13/001* (2013.01); *C12R 1/225* (2013.01); *C12R 1/24* (2013.01); *C12R 1/25* (2013.01); *A61K 38/00* (2013.01); *A61K 2035/115* (2013.01); *C12N 1/00* (2013.01)

(58) Field of Classification Search
CPC ....... C12P 13/001; A61K 35/747; A61K 8/99; A21D 8/04; A61Q 19/00; A61Q 19/08; C12R 1/24; C12R 1/25; C12R 1/225; A23L 33/135
See application file for complete search history.

(56) References Cited

U.S. PATENT DOCUMENTS

2015/0292048 A1  10/2015  Mayer

FOREIGN PATENT DOCUMENTS

| JP | 2009543576 A | 12/2009 |
| WO | 2008010252 A2 | 1/2008 |
| WO | 2014/072408 A1 | 5/2014 |

OTHER PUBLICATIONS

De Angelis et al., "Molecular and functional characterization of Lactobacillus sanfranciscensis strains isolated from sourdoughs", International Journal of Food Microbiology, 2007, vol. 114, No. 1, pp. 69-82.

Di Cagno et al., "Genotypic and phenotypic diversity of Lactobacillus rossiae strains isolated from sourdough", J. Appl. Microbiol., 2007, vol. 103, pp. 821-835.

Siragusa et al., "Taxonomic Structure and Monitoring of the Dominant Population of Lactic Acid Bacteria during Wheat Flour Sourdough Type I Propagation Using Lactobacillus sanfranciscensis Starters", Appl. Environ. Microbiol., 2009, vol. 75, No. 4, pp. 1099-1109.

Vogel et al., "Genomic analysis reveals Lactobacillus sanfranciscensis as stable element in traditional sourdoughs", Microbial Cell Factories, 2011, vol. 10, No. 10, Suppl. 1, S6, pp. 1-11.

Notification of Reasons for Rejection cited in Patent Application No. 2015-555745, dated Dec. 5, 2017, 9 pgs.

(Continued)

*Primary Examiner* — Robert J Yamasaki
*Assistant Examiner* — Charles Z Constantine
(74) *Attorney, Agent, or Firm* — Rothwell, Figg, Ernst & Manbeck, P.C.

(57) ABSTRACT

The invention relates to acetylcholine-producing microorganisms for use in the prevention and/or treatment of intestinal diseases, and/or reduction of risks of intestinal diseases, and/or improvement of intestinal health as well as promoting healthy gut flora. The acetylcholine-producing microorganisms may be provided as a pharmaceutical dosage form or as additive to functional food or food supplemental products. Also encompassed is a method for the production of acetylcholine by use of Lactobacilli. Further the invention refers to microbially produced acetylcholine for use in the treatment and/or prevention of intestinal diseases.

15 Claims, 18 Drawing Sheets

(56) References Cited

OTHER PUBLICATIONS

Communication pursuant to Article 94(3) EPC cited in corresponding application No. 14 702 835.5 dated Dec. 19, 2016, 8 pages.
Murakami et al., "The effect of Lactobacillus brevis KB290 against irritable bowel syndrome: a placebo-controlled double-blind cross-over trial", Biophysco Social Medicine, 2012, 6:16, 8 pages.
Search Report of the European priority application EP 13 153 996.7, dated Jun. 14, 2013, 8 pgs.
International Search Report cited in PCT/EP2014/052129, dated Mar. 7, 2014, 2 pgs.
Herbert "How to Start A Sourdough Culture" The Guardian, Feb. 20, 2012.
Chavan "Sourdough Technology—A Traditional Way for Wholesome Foods: A review" Comprehensive Reviews in Food Science and Food Safety vol. 10 2011.
Thom ("Healthy Bread Recipes" Thom's Recipe File, 2005, available at www.thomcooks.com/healthy-bread-recipes.htm).
Stephenson ("The production of Acetylcholine by a Strain of Lactobacillus plantarum" Journal of General Microbiology (Now called Microbiology), 1947, 1, 279-298).
Ducrotte Philippe et al: "Clinical trial: Lactobacillus plantarum 299v (DSM 9843) improves symptoms of irritable bowel syndrome.", World Journal of Gastroenterology : WJG Aug. 14, 2012, vol. 18, No. 30, Aug. 14, 2012 (Aug. 14, 2012), pp. 4012-4018, XP002697271, ISSN: 1007-9327.
Shen J et al: "Meta-analysis: the effect and adverse events of Lactobacilli versus placebo in maintenance therapy for Crohn disease.", Internal Medicine Journal Feb. 2009,vol. 39, No. 2, Feb. 2009 (Feb. 2009), pp. 103-109, XP002697272, ISSN: 1445-5994.
Lyte Mark: "Probiotics function mechanistically as delivery vehicles for neuroactive compounds: Microbial endocrinology in the design and use of probiotics", Bioessays, vol. 33, No. 8, Aug. 2011 (Aug. 2011), pp. 574-581, XP002677196.
Stanaszek P M et al: "Isolation Extraction and Measurement of Acetylcholine From Lactobacillus Plantarum", Applied and Environmental Microbiology, vol. 34, No. 2, 1977, pp. 237-239, XP002697274, ISSN: 0099-2240.
Price W E et al: "Effects of acetylcholine on intestinal blood flow and motility", American Journal of Physiology 1969, vol. 216, No. 2, 1969, pp. 343-347, XP009169705, ISSN: 0002-9513.
Dissertation of the inventor Anna Zhenchuk entitled "Bio-Functionality of Sourdough Metabolites in Healthy and Inflamed Gastro-Intestinal Tract". The dissertation was submitted to the Technical University in Munich on Dec. 4, 2013. 95 pages.

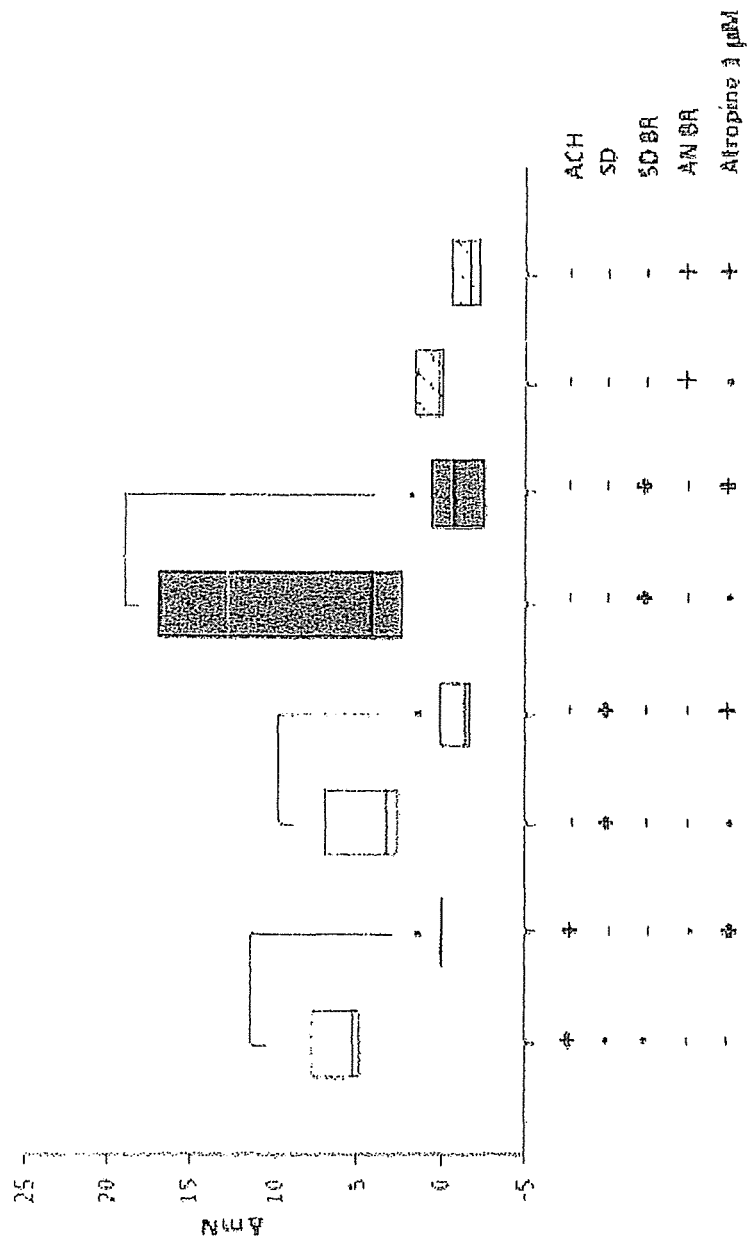

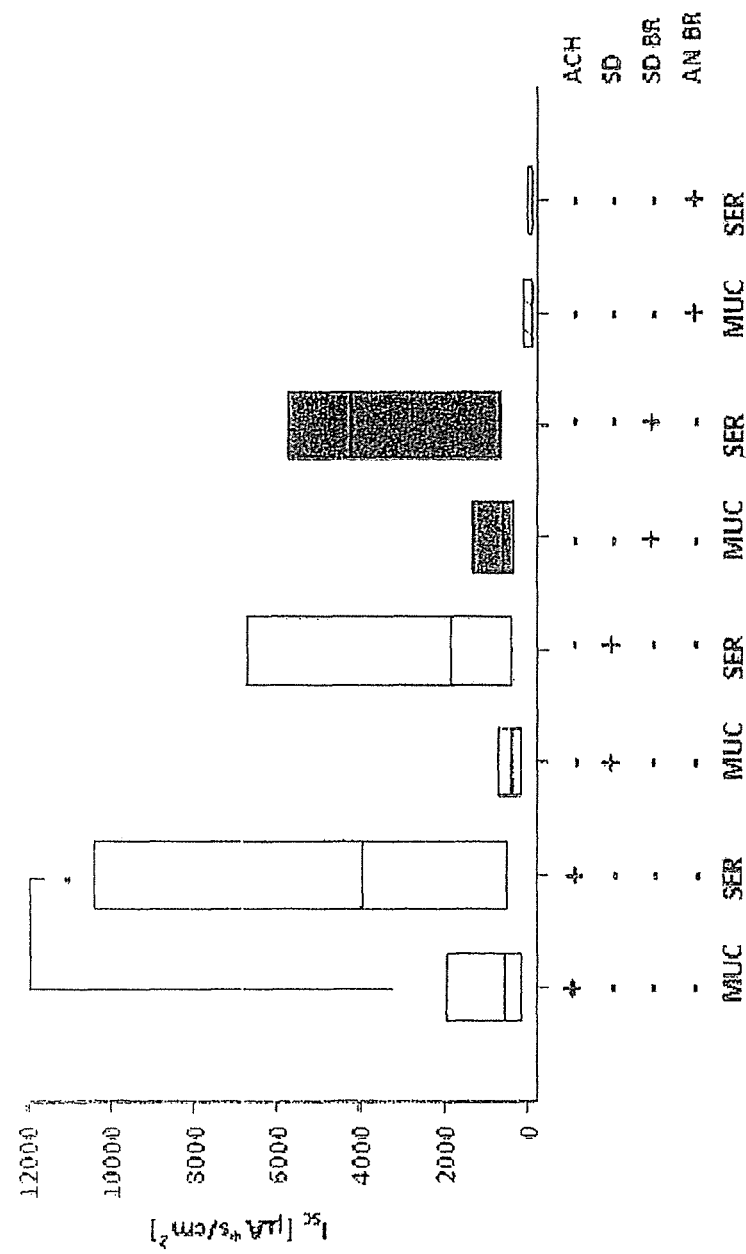

USE OF MICROORGANISMS FOR THE PREVENTION AND TREATMENT OF INTESTINAL DISEASES

This application is a division of U.S. Ser. No. 14/765,682, filed Aug. 4, 2015, which is a 35 U.S.C. 371 National Phase Entry Application from PCT/EP2014/052129, filed Feb. 4, 2014, which claims the benefit of European Patent Application No. 13153996.7 filed on Feb. 5, 2013, the disclosure of which is incorporated herein in its entirety by reference.

DESCRIPTION

The invention relates to acetylcholine-producing microorganisms for use in the prevention and/or treatment of intestinal diseases, and/or reduction of risks of intestinal diseases, and/or improvement of intestinal health as well as promoting healthy gut flora. The acetylcholine-producing microorganisms may be provided as a pharmaceutical dosage form or as additive to functional food or food supplemental products. Also encompassed is a method for the production of acetylcholine by use of Lactobacilli. Further the invention refers to microbially produced acetylcholine for use in the treatment and/or prevention of intestinal diseases.

A large number of patients suffer from gastrointestinal disorders associated with the lower small bowel and/or large bowel. These disorders include irritable bowel syndrome (IBS), or spastic colon, idiopathic alterative colitis, mucous colitis, collagenous colitis, Crohn's disease, inflammatory bowel disease in general, microscopic colitis, antibiotic-associated colitis, idiopathic or simple constipation, diverticular disease, and AIDS enteropathy.

Irritable bowel syndrome is the most common of all gastrointestinal disorders, affecting 11-14% of adults and accounting for more than 50% of all patients with digestive complaints. (G. Triadafilopoulos et al., Bowel Dysfunction in fibromyalgia, Digestive Dis., Sci. 36 (1): 59-64 [1991]; W. G. Thompson, Irritable Bowel Syndrom: Pathogenesis and Management, Lancet, 341:1569-1572 [1993]). It is thought that only a minority of people with IBS actually seek medical treatment. Patients with IBS present with disparate symptoms, for example, abdominal pain, predominantly related to defecation, alternating diarrhea and constipation, abdominal distention, gas, and excessive mucus in the stool. There are three groups of IBS: constipation-predominant IBS (C-IBS), alternating IBS (A-IBS) and diarrhea-predominant IBS (D-IBS). IBS is recognized as a chronic condition, which may have profound effect on the patient's quality of life.

A number of possible causes for IBS have been proposed such as fiber-poor Western diet, intestinal motility malfunction, abdominal pain perception, abnormal psychology or behavior, or psycho-physiological response to stress. However, none of those causes has been fully accepted (W. G. Thompson [1993] supra).

Patients suffering from IBS appear to perceive normal intestinal activity as painful. For example, IBS patients experience pain at lower volumes of rectal distention than normal or have lower than normal threshold for perceiving migrating motor complex phase III activity (W. E. Whitehead et al., Tolerance for Rectosigmoid Distention in Irritable Bowel Syndrom, Gasteroenterol. 98:1187-92 [1990]; J. E. Kellow et al., Enhanced Perception of Physiological Intestinal Motility in the Irritable Bowel Syndrom, Gasteroenterol. 101 (6):1621-24 [1991]).

Bowel motility in IBS patients differs from a normal controlled response to various stimuli such as drugs, hormones, food, and emotional stress (D. G. Wangel and D. J. Deller, Intestinal Motility in Man, III: Mechanisms of Constipation and Diarrhea with Particular Reference to the Irritable Bowel, Gasteroenterol. 48: 69-84 [1965]; R. F. Harvey and A. E. Read, Effect of Cholecystokinin and Colon Motility and on Symptoms of Patients with Irritable Bowel Syndrome, Lancet i: 1-3 [1973]; R. M. Valori et al., Effects on Different Types of Stress and "Prokinetic drugs" on the Control of the Fasting Motor Complex in Humans, Gasteroenterol. 90: 1890-900 [1986]).

Evans et al. and Govath and Farthing recognized that irritable bowel syndrome is frequently associated with disordered gastro-intestinal motility. (P. R. Evans et al., Gastroparesis and Small Bowel Dysmotility in Irritable Bowel Syndrome, Dig. Dis. Sci. 42 (10): 2087-93[1997]; D. A. Gorard and M. J. Farthing, Intestinal Motor Function in Irritable Bowel Syndrome, Dig. Dis. 12 (2): 72-84[1994]). Treatment directed to bowel dysmotility in IBS includes the use of serotonine antagonists (D. P. Becker et al., Mesoazacyclic Aromatic Acid Amides And Esters as Serotonergic Agents, U.S. Pat. No. 5,612,366; M. Ohta et al., Methods for Treatment of Intestinal Diseases, U.S. Pat. No. 5,547,961) and Choleocytokinin antagonists (Y. Sato et al., Benzodiazepine derivatives, U.S. Pat. No. 4,970,207; H. Kitajima et al., Thienylazole Compound and Thienotriazolodiazepine Compound, U.S. Pat. No. 5,760,032). Colonic motility index, altered myoelectrical activity in the colon and small intestinal dysmotility, however, have not proven to be reliable diagnostic tools because they are not IBS-specific (W. G. Thomson [1993], supra).

Administration of probiotics for the treatment of IBS has been attempted. For example, Allan et al. described the use of a strain of *Enterococcus faecium* to alleviate symptoms. (W. D. Allan et al., Probiotic Containing *Enterococcus faecium* strain NCIMB 40371 U.S. Pat. No. 5,728,380 and Probiotic, U.S. Pat. No. 5,589,168). Borody taught a method of treating irritable bowel syndrome by at least partial removal of the intestinal microflora by lavage and replacement with a new bacteria community introduced by fecal inoculum from a disease-screened human donor or by a composition comprising *Bacterioids* and *Escherichia coli* species. (T. J. Borody, Treatment of Gastro-Intestinal Disorders with a Fecal Composition of Bacterioids and *E. coli*, U.S. Pat. No. 5,443,826).

It is a contention of many scientists that the health and well-being of people can be positively or negatively influenced by the microorganisms which inhabit the gastrointestinal tract, and in particular the large intestine. These microorganisms, through the production of toxines, metabolic by-products and short-chain fatty acids, and the like, affect the physiological condition of the host.

The constitution and quantity of the gut microflora can be influenced by conditions or stress induced by disease, lifestyle, travel and other factors. If microorganisms which positively effect health and well-being of the individual can be encouraged to populate in the large bowel, this should improve the psychological well-being of the host.

The introduction of beneficial microorganisms or probiotics may be accomplished by ingestion of the organisms in drinks, yogurts, capsules, and other forms allowing viable organisms to arrive at the large bowel.

However, until now, no reliable method has been found or developed to stimulate the enteric nervous system (ENS) which regulates the intestinal bowel movements and secretory functions of epithelial layer in a sufficient manner.

The problem of the present invention was therefore to provide a method to intervene in the regulation of the intestinal bowel movements and secretory functions of epithelial layer in a sufficient manner to influence thereby the course of intestinal diseases.

The inventors of the present invention have conducted intensive studies and found as a result that intestinal function can be modulated by acetylcholine-producing microorganisms. Thereby a method for the targeted dual stimulation of motility and secretion by acetylcholine in the intestine through selection and specific administration of acetylcholine-producing microorganism, particularly lactic acid bacteria is provided. This treatment method is a promising alternative or addition to known therapies for chronic IBS and other disorders associated with impaired intestinal motility and secretion.

A first aspect of the present invention is therefore an acetylcholine-producing microorganism for the use in the prevention and/or treatment of intestinal diseases and/or reduction of risk of developing intestinal diseases.

A further aspect of the present invention is the non-medical use of an acetylcholine-producing microorganism for the maintenance and/or improvement of intestinal health, particularly for the improvement of intestinal health.

The acetylcholine-producing microorganism is a live organism and preferably capable of propagating in the intestinal area.

The term "intestinal area" as used herein is intended to include the small intestine and large intestine. Large intestine is intended to include the colon and rectum, and in humans, is intended to include the colon, rectum and caecum.

The term "reduction of risk of developing intestinal diseases" as used herein means that an individual being treated with the acetylcholine-producing microorganism of the present invention exhibits a lower risk to develop an intestinal disease caused by external stimuli or physiological processes compared to a non-treated individual.

The term "maintenance and/or improvement of intestinal health" as used herein means that an individual, upon treatment with the acetylcholine-producing microorganism, exhibits a different gut flora, which is beneficial for human or animal health and reasonable for a maintenance and/or an improvement of the digestion of said individual. The improved gut flora further may lead to an increased resistance of the subject to develop an intestinal disease by out-competing harmful bacteria and stimulating the normal bowel movement.

The term "microorganism" as used herein comprises bacteria and yeasts. The bacteria are preferably Lactobacillaceae such as *Lactobacillus* strains, in particular *Lactobacillus sanfranciscensis* strains, *Lactobacillus rossiae* strains, *Lactobacillus lactis* and *Lactobacillus plantarum* (Stephenson et al., The production of acetylcholine by a strain of *Lactobacillus plantarum*, Microbiology 1947, Vol 1, No 3, 279-298).

In certain embodiments, the microorganism is not a *Lactobacillus plantarum* strain, particularly not *Lactobacillus plantarum* strain 299v (DSM 9843), or *Lactobacillus plantarum* strain (ATCC 10241). In certain embodiments, the microorganism is not a *Lactobacillus rhamnosus* strain, particularly not *Lactobacillus rhamnosus* GG.

The intestinal diseases encompass inflammatory bowel diseases (IBD), such as ulcerative colitis, Crohn's disease, collagenous colitis, lymphocytic colitis, ischaemic colitis, Behget's disease, indeterminate colitis, diversion colitis, pouchitis or microscopic colitis and/or colon cancer and/or diseases associated with microorganisms, such as candidiasis, small intestinal bacterial overgrowth, acute or chronic bowel infections, and/or diseases induced by sulphate-reducing bacteria, and/or intestinal diverticular, and/or intestinal carcinoma, and/or functional bowel disorders (FBD) such as irritable bowel syndrome, and/or disorders associated with the secretions of the intestinal wall controlled by the enteronervous system.

The term "Functional bowel disorder" (FBD) refers to gastro-intestinal disorders which are chronic or semi-chronic and which are associated with bowel pain, disturbed bowel function and social disruption. Particular combinations and prevalence of symptoms characterize in following seven FBD subgroups, which are defined in accordance with the classification system known as the "Rome criteria": 1) C1: constipation-predominant irritable bowel syndrome; 2) C1: diarrhea-predominant irritable bowel syndrome; 3) C3: Functional constipation; 4) C4: Functional diarrhea; 5) C2: Functional abdominal bloating; 6) F3a: Pelvic Floor dyssynergia; 7) F3b: internal anal sphincter dysfunction.

More specifically, the intestinal disease may be a functional intestinal disorder and/or a disorder associated with the secretions of the intestinal wall controlled by the enteric nervous system, in particular functional constipation, functional diarrhea and/or irritable bowel syndrome (IBS), such as particular constipation-predominant IBS, alternating IBS or diarrhea-predominant IBS.

The acetylcholine-producing microorganism of the present invention is preferably useful for maintaining and/or promoting a healthy gut flora and/or reducing the toxic effects of the digestive process and/or stimulating the digestive system and/or improving intestinal control. The promotion of a healthy gut flora leads to an out-competing of the harmful bacteria in the intestines, in particular the large intestine, and more particularly the colon, and thereby reducing the toxic effect of the digestive process, stimulating the digestive system and improving bowel control.

The acetylcholine-producing microorganism of the present invention is preferably useful for modulating the course of inflammatory bowel diseases (IBD) in a beneficial way and relieving the symptoms of IBD patients by inhibition of the secretion of pro-inflammatory chemokine IP-10.

In another embodiment, the intestinal disease may be an inflammatory bowel disease. The diseases are preferably ulcerative colitis, Crohn's disease, collagenous colitis, lymphocytic colitis, ischaemic colitis, Behget's disease, indeterminate colitis, diversion colitis and/or microscopic colitis. The diseases are more preferably ulcerative colitis and/or Crohn's disease.

The microorganism of the present invention is capable of producing acetylcholine. Preferably, the acetylcholine-producing microorganism produces ≥20, 25, 30, 35 or 40 mg/kg acetylcholine under suitable culture conditions as described, more preferably ≥40 mg/kg and even more preferably ≥35 mg/kg. Any culture medium might be used for the culture of the acetylcholine-producing microorganisms, which are suitable for Lactobacilli-culture. Preferably, MRS-broth is used as a culture medium. Preferably, the acetylcholine concentration is adjusted to a $10^6$/ml bacteria count.

The acetylcholine-producing microorganism is preferably a bacterium. More preferably, the bacterium is a Lactobacillaceae such as a *Lactobacillus* strain, in particular a *Lactobacillus sanfranciscensis* strain, *Lactobacillus rossiae* strain, *Lactobacillus brevis* strain, or *Lactobacillus plantarum* strain, which are generally available from the public catalogue of Deutsche Sammlung von Mikroorganismen und Zellkulturen GmbH (Braunschweig, Germany).

In a more preferred embodiment, the *Lactobacillus* strain is selected from any one of strains DSM 26024, DSM 23090, DSM 23091, DSM 23200, DSM 23092, DSM 23093, DSM 23201, DSM 23174 and DSM 23121 or a strain cultivated therefrom, more particularly strain DSM 23090 or DSM 23093 or a strain cultivated therefrom. These strains have been deposited at the Leibnitz-Institut DSM—Deutsche Sammlung von Mikroorganismen und Zellkulturen GmbH (Braunschweig, Germany), according to the Budapest Treaty. The novel *Lactobacillus* strains have the following accession numbers and deposition dates: DSM 23090 (2012 Jun. 21), DSM 23091 (2012 Jun. 21), DSM 23200 (2012 Jun. 21), DSM 23092 (2012 Jun. 21), DSM 23093 (2012 Jun. 21), DSM 23201 (2012 Jun. 21), DSM 26024 (2012 Jun. 4), DSM 23174 (2012 Jun. 21), DSM 23121 (2012 Jun. 21).

The term "strain cultivated therefrom" as used herein refers to offspring strains derived by cultivation of the original strain.

The acetylcholine-producing microorganism is preferably an acetylcholine-secreting microorganism. The term "acetylcholine-secreting microorganism" as used herein means that the microorganism secrets acetylcholine into the culture medium.

The present invention refers to the medical use of an acetylcholine-producing microorganism. Preferably, the microorganism is provided as a pharmaceutically acceptable dosage form or in form of a nutrient, e. g. food or beverage.

In one embodiment, the acetylcholine-producing microorganism is provided in a pharmaceutical composition. The acetylcholine-producing microorganisms can also be provided as an additive in a functional food or in a functional beverage. The pharmaceutical composition, food or beverages, incorporating the microorganism can be safely consumed and are especially recommended for subjects perceived to be at risk or suffering from gastro-intestinal dysfunction or organic disorders or diseases, e.g. conditions or symptoms related to IBS, or IBD. They contain the acetylcholine-producing microorganism preferably in an effective amount to treat or prevent said disorders or diseases.

As used herein, the term "an effective amount" refers to an amount effective to achieve a desired therapeutic effect, such as treating and/or preventing diseases, conditions and symptoms related to IBS or IBD.

The effective amount of the acetylcholine-producing microorganisms preferably comprises a dosage in the range of $10^6$ to $10^{12}$ cfu/dosage form (colony forming units/dosage form), more preferably in the range of $10^7$ to $0.5 \times 10^{12}$ cfu/dosage form, even more preferably in the range of $10^9$ to $10^{11}$ cfu/dosage form. The dosage form may be administered once or several times, e. g. 2, 3 or more times daily.

The pharmaceutical composition may be in liquid or solid form. The composition contains at least one of the acetylcholine-producing microorganisms or a mixture thereof and optionally a pharmaceutically acceptable carrier.

The amount of, e. g. microorganisms, incorporated into a pharmaceutical composition may vary from about 0.1 to about 100% by weight, preferably from about 2 to about 20% by weight, even more preferably from about 4 to about 10% by weight, based on the total weight of the composition.

The pharmaceutical composition of the present invention can be made in the usual pharmaceutical forms known in literature, such as for example tablets, coated tablets, capsules, packets, solutions, suspensions, emulsions, suppositories, pellets, syrups, vaginal suppositories, ointments, creams and so on. Preferably the composition comprises an enteric coating. They can be prepared in the usual manner by mixing the active ingredient with excipients and/or carriers, optionally adding adjuvants and/or dispersing agents. Should water be used as a diluent, also other organic solvents can be used in the form of adjuvants. Adjuvants can be e. g. water, non-toxic organic solvents such as paraffins, vegetable oils (peanut oil or sesame oil), alcohols (e. g. ethanol, glycerol), glycols (propylene glycol, polyethylene glycol). Solid carriers can be e. g. natural mineral flours (kaolin, talc), synthetic mineral flours (e. g. silicates), sugar (e. g. cane sugar). Emulsifiers can be alkyl sulphonates or aryl sulphonates and the like, dispersers e. g. lignin, methyl cellulose, starch and polyvinyl pyrrolidine and lubricants e. g. magnesium stearate, talc, stearic acid, sodium lauryl sulphonate.

The composition may contain the acetylcholine-producing microorganisms lyophilized, pulverized and powdered, optionally for reconstitution in a pharmaceutically acceptable liquid carrier administered to intestinal area, e. g. oral, rectal or naso-duodenal. The administration takes place in the usual manner, preferably by oral/rectal route. It may then be infused, dissolved such as in saline, as an enema. As a powder, it can preferably be provided in a palatable form for reconstitution for drinking. The powder may also be reconstituted to be infused via naso-duodenal infusion.

Pharmaceutical forms adapted to this end can contain, in addition to usual excipients such as lactulose, dextrose, lactose, other additives such as sodium citrate, calcium carbonate, calcium dihydrogen phosphate, together with several additional substances such as starch, gelatin and the like. In case of liquid forms compatible coloring agents or flavoring substances may be added.

Further components of the composition containing the acetylcholine-producing microorganism may include an active agent, e. g. glutamin/glutamate or precursors thereof, mannans, galacturonic acid oligomers, herbal extracts such as Regulat® (registered trademark of Dr Niedermayer Pharma) and Iberogast® (registered trademark of Steigerwald Arzneimittelwerk GmbH), chokeberry beer yeast, a drug useful for the treatment of ulcerative colitis, such as sulphasalazine, 5-ASA agents, corticosteroids, such as adrenal steroid, prednisone, hydrocortisone, or budesonide, or drugs used against pain, diarrhea, infection or IBS such as serotonine-4 receptor agonist, e. g. tegaserod. The composition can be combined with other adjuvants such as antacids to dampen bacterial inactivation in the stomach. Acid secretion in the stomach could also be pharmacologically suppressed using H2 antagonists or omeprazole.

The composition of the invention may be provided in the form of a kit for separate sequential or simultaneous administration in conjunction with such active agents as described herein above. These active agents may conveniently be formulated together with the composition of the invention in standard pharmaceutical dosage forms, e. g. in combination with at least one pharmaceutically acceptable carrier.

In another preferred embodiment, a composition containing the acetylcholine-producing microorganism can contain at least one additional microorganism, i.e. non-acetylcholine-producing microorganism such as a bacterium for maintaining and/or restoring favorable gut flora. The additional bacteria are preferably pro-biotic bacteria.

In another embodiment of the invention, the acetylcholine-producing microorganisms can preferably be provided as a probiotic, preferably as an additive to functional food or to functional beverages.

The amount of the microorganisms as a nutrient additive may vary from about 0.0001 to about 20% by weight, preferably from about 0.01 to about 10% by weight and even more preferably from about 0.1 to about 5% by weight.

In another preferred embodiment the acetylcholine-producing microorganisms can be applied to an edible material, preferably a food—or feed product such as cereals, in particular oat flakes or bread, a beverage or dairy products, in particular yogurt, sauerkraut juice, plant extracts such as Regulat®, fermented beverages or Brottrunk®. The application to the edible material may be achieved by coating said material with the acetylcholine-producing microorganisms, preferably by spraying the microorganisms onto the edible material. The acetylcholine-producing microorganisms can also be applied by injecting them into an edible material, such as bread, yogurt, or cheese, preferably sour dough bread.

The term "functional food" as used herein is food, which, in addition to its nutritional and sensory functions, has a positive effect on the metabolism and, within a balanced nutrition, contributes to an improvement of health, an increase in wellbeing and/or a reduction of health risks. The functional food may be a natural food or a food which has been altered by adding or cutting off a component.

In a preferred embodiment, the functional food is a fermented product, more preferably, the functional food is sour dough or sour dough bread.

The sour dough bread of the present invention has the advantage that it may not only contain the acetylcholine-producing strains, but in addition also high contents of other acetylated compounds such as N-acetyl-glycine, homoserine, canavanine, and the like.

The term "functional beverage" as used herein is a beverage, which in addition to its nutritional and sensory function, has a positive effect on the metabolism and, within a balanced nutrition, contributes to an improvement of health, an increase in wellbeing and/or a reduction of health risks. It takes its effect within normal food habits in an amount common for consumption. The functional beverage may comprise additional components such as herbs, vitamins, minerals, aminoacids, or additional other food or vegetable ingredients to provide specific health benefits that go beyond general nutrition. Alternatively, it may include stimulants such as taurin, glucoronolactone, caffeine, B-vitamins, guarana, ginseng, gingko biloba, L-carnitine, sugars, antioxidants, yerba mate, creatine, milk thistle and the like. In a preferred embodiment, it additionally contains a prebiotic suitable to be digested by the acetylcholine-producing microorganisms of the present invention.

A preferred functional beverage is a drinking yogurt, a fermented grain beverage, alcohol-free beer, Brottrunk®, fruitjuice-based beverages or beverages containing plant or herbal extracts such as Iberogast®.

The functional food or functional beverage can preferably also be administered with at least one additional active agent for the treatment of intestinal diseases. The additional active agent can be selected from the group of medicaments as described above.

In another embodiment the active agent may preferably be at least one additional bacterium for maintaining and/or restoring a favorable gut flora. The additional bacterium can be selected form the group of probiotic bacteria.

Preferred pro-biotic bacteria can be selected from the group comprising Strains from *Lactobacillus* and *Bifidobacterium* such as *Lactobacillus acidophilus, Lactobacillus johnsonii, Lactobacillus casei, Lactobacillus lactis, Lactobacillus reuteri, Lactobacillus rhamnosus* and/or *Bifidobacterium lactis*.

Optionally, the composition can also contain a prebiotic. As used herein, a "prebiotic composition" is an at least non-digestible food ingredient that beneficially affects the host by selectively stimulating the growth, activity or both of one of a limited number of species of microorganisms already resident in the colon. The prebiotic is preferably a non-digestible oligosaccharide such as fructo-oligosaccharides, galacto-oligosaccharides, lactolose, xylo-oligosaccharides, isomalto-oligosaccharides, soy bean oligosaccharides, gentio-oligosaccharides, gluco-oligosaccharides, fructans, lactosuccrose, short-chain fructo-oligosaccharides, and mixtures thereof.

The present invention also provides a method for the production of acetylcholine by use of Lactobacilli. Preferably, a single *Lactobacillus* strain is used or a combination of *Lactobacillus* strains or a composition of *Lactobacillus* strains. The *Lactobacillus* strains used therefore are in particular *Lactobacillus sanfranciscensis* strains, *Lactobacillus rossiae* strains, *Lactobacillus brevis* strains, or *Lactobacillus plantarum* strains, more particularly strain DSM 26024, DSM 23090, DSM 23091, DSM 23200, DSM 23092, DSM 23093, DSM 23201, DSM 23174 and DSM 23121 or a strain cultivated therefrom, even more particularly strains DSM 23090 or DSM 23093.

Another aspect of the present invention is microbially produced acetylcholine for use in the treatment and/or prevention of intestinal diseases as described above. The acetylcholine may be produced preferably by the microorganisms of the invention. The microorganisms are preferably Lactobacillaceae such as *Lactobacillus* strains, in particular *Lactobacillus sanfranciscensis* strains, *Lactobacillus rossiae* strains, *Lactobacillus brevis* strains, or *Lactobacillus plantarum* strains. The intestinal diseases encompass the intestinal diseases described above such as inflammatory bowel diseases or functional bowel disorders. Preferably, the disease is irritable bowel syndrome and/or disorders associated with secretions of the intestinal wall controlled by the enteronervous system. The microbially produced acetylcholine may be administered orally, e.g. added to food and/or feed products. The addition may occur during the manufacture of the food and/or feed product by using the microorganisms of the invention also for the fermentation of the food and/or feed product. Such a fermented food product might be sour dough bread, wherein the live microorganisms are killed during the baking phase by heat, resulting in a sour dough bread containing acetylcholine produced by the microorganisms. The content of the microbial produced acetylcholine is in a range of about 5 to 1000 mg acetylcholine/kg food or feed product, preferably in a range from about 20 to 500 mg acetylcholine/kg feed product or food product, more preferably in a range from about 40-200 mg acetylcholine/kg feed product or food product. Preferably, the amount of acetylcholine equates to the recommended daily dosage.

Figure 1A:
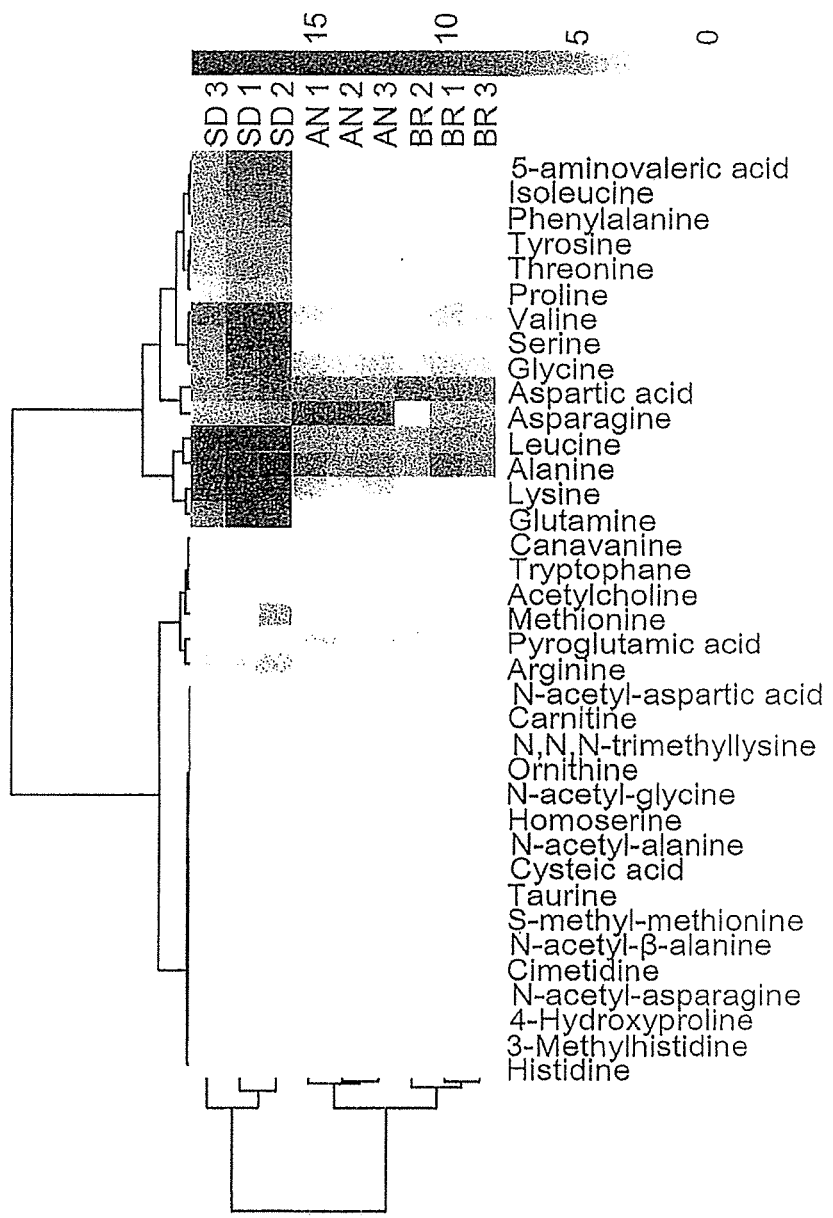
FIGS. 1A-1B: Metabolite profile in water extracts of sourdough, sourdough bread and analog bread. A: Heatmap of absolute metabolite concentrations in water extract from sourdough (SD), sourdough bread (BR) and analog bread (AN) in triplicates. Water extracts constitute 5-10% of total dough or bread dry mass. B: Principal component analysis (PCA) of metabolites reveals significant differences in metabolite concentrations between sourdough (SD), sourdough bread (BR) and analog bread (AN).

Further, the invention shall be explained in more detail by the following examples.

EXAMPLES

1) Methods and Materials
1.1) Sourdough and Bread

Sourdough (Vollsauer) was prepared by traditional propagation of type I sourdough rye starter containing the Lactobacilli strains DSM 26024, DSM 23090, DSM 23091, DSM 23200, DSM 23092, DSM 23093, DSM 23201, DSM 23174 and DSM 23121. The composition of sourdough and sourdough bread is: 71% rye flour, 25% wheat flour, 1.8% salt and 2% bread crumbs (pH 4.5, acidity 9-10). The dough was baked at 298° C. for 1.5 hours. Analog bread was identical to sourdough bread with substitution of sourdough starter with 2.5% sodium bicarbonate, 0.13% acetic acid and 1.2% lactic acid.

1.2) Metabolite Analysis

Water extracts (<10 kDa) of sourdough, sourdough bread and analog bread as well as MRS growth media of lactic acid bacteria were subjected to LC-MS/MS analysis for metabolite quantification. MRS media was filtered with 10 kDa Vivaspin 500 filters (Sartorius Stedim biotech, Goettingen, Germany) before analysis.

Samples were measured using:
Dionex Ultra High Performance Liquid Chromatography UltiMate® 3000 (Dionex, Idstein, Germany)
Pump—HPG-34005D
Degasser—SRD-3400
Autosampler—WPS-3000TSL
Column oven—TCC-30005D
API 4000 QTRAP, Linear Ion Trap Quadrupole Mass Spectrometer (AB Sciex, Darmstadt, Germany):
Ionization type—electrospray ionization (ESI)
Instrument control—Analyst software (AbSciex, Darmstadt, Germany)
Stationary phase: TSKgel Amide-80 3 µm (150×2 mm, Tosoh Bioscience, Stuttgart, Germany)
Stationary phase temperature: 40° C.
Mobile phase: eluent A: acetonitrile/5 mM/L ammonium acetate in water (95+5)
eluent B: 5 mM/L ammonium acetate in water (95+5)

| gradient: | 0 min | 90% A | 10% B |
|---|---|---|---|
|  | 5 min | 90% A | 10% B |
|  | 10 min | 80% A | 20% B |
|  | 15 min | 50% A | 50% B |
|  | 18 min | 0% A | 100% B |
|  | 21 min | 0% A | 100% B |
|  | 24 min | 90% A | 10% B |
|  | 30 min | 90% A | 10% B |
| flow: | 200 µl/min |  |  |

The Chromatograms were analysed with Multiquant 2.0 (AB Sciex, Darmstadt, Germany) and concentrations in the samples were calculated according to the spectra of standards.

1.3) Extraction

Sourdough, sourdough bread and analog bread were freeze-dried and grinded into powder. 100 g of powdered bread or sourdough was solubilized in 500 mL distilled water and extracted for 3 hours at 50° C. with constant stirring. The suspension was centrifuged at 9000 rpm for 20 min. The supernatant was collected and kept at 4° C. The pellet was re-suspended again in 500 mL distilled water and 3 hour extraction repeated. After centrifugation the pellet was again re-suspended in 500 mL distilled water and extracted overnight. Supernatants after three extraction steps (total volume of approx. 1.5 L) were pooled together and step-wise filtered using Vivaflow 200 cassettes of 0.2 µm, 100 kDa and 10 kDa exclusion thresholds (Sartorius, Goettingen, Germany). The filtrates of the 100 kDa and 10 kDa exclusion thresholds were freeze dried and re-suspended in distilled water to 25% for in vitro assays. 10 g of <10 kDa fraction was extracted from 100 g freeze-dried bread and sourdough.

1.4) Endotoxin Measurement and Clean-Up

Endotoxin concentrations measurement in water extracts from sourdough, sourdough bread and analog bread were determined using Limulus Amebocyte Lysate (LAL) Chromogenic Endpoint Assay (Hycult biotech, Uden, Netherlands). The assay was performed according to the manufacturer's instructions. Endotoxin contamination in water extracts from sourdough, sourdough bread and analog bread was removed using Detoxi-Gel™ Endotoxin Removing Columns (Thermo Scientific, Rockford, USA), containing a resin with immobilized polymyxin B to bind and remove pyrogens from solution. The removal of endotoxin was performed according to the manufacturer's instructions.

1.5) ELISA

Interferon inducible protein (IP-10) (murine/human) and (murine) concentrations in cell culture supernatants were determined using the appropriate ELISA kits (R&D Europe, Abington, England) according to the manufacturer's instructions. The ELISA was performed using Nunc MaxiSorp® flat-bottom 96 well plates (Greiner Bio-One GmbH, Frickenhausen, Germany). Briefly 96-well plates were coated with the appropriate capture antibody overnight at RT. Plates were washed 3 times with phosphate buffered saline (PBS), blocked with 1% bovine serum albumin in PBS and incubated with cell culture supernatants for 1.5 h at RT. Plates were washed and incubated with the appropriate detection antibody for 1.5 h at RT. Plates were washed and incubated with a detection enzyme. Plates were washed and incubated with a substrate solution. Protein concentration was determined by photometrical analysis of the reaction of substrate and detection enzyme.

1.6) Bacterial Culture

*L. sanfranciscensis* strains (DSM 23090, DSM 23091, DSM 23092, DSM 23093, DSM 23174, DSM 23200, DSM 23201) and *L. rossiae* (DSM 26024) isolated from sourdough, *L. sanfranciscensis* type strain DSM 20451 (DSMZ GmbH, Braunschweig, Germany), *L. plantarum* FUA 3038 and *L. brevis* 3113 (provided by Prof. Ganzle from University of Alberta, Canada), *L. paracasei* VSL #3 (provided by Dr. DeSimone, L'Aquila, Italy) were grown at 30° C. in MRS broth (pH 5.4) containing freshly added 0.15% L-cystein under anaerobic conditions using Anaerogen packages (Anaerogen, Basingstoke, Oxoid, UK). Fixed bacteria (5% formaldehyde, 4 hours, 4° C.) were washed three times with sterile PBS before use. Concentrated conditioned media (CM) were generated by transferring bacteria ($5 \times 10^7$ cfu/ml) from anovernight culture to DMEM (1% glutamine, 20 mM HEPES) and anerobical cultivation overnight at 30° C. Bacteria and bacterial supernatant (CM) were separated after centrifugation (4500 g, 10 min, RT). CM was adjusted to pH 7.4, filter sterilized (0.22 µm), and concentrated (100×) using Vivacell filter systems with an exclusion size of 100 kDa (Satorius Stedim Biotech, Goettingen, Germany). Concentrated conditioned media was diluted to 1× in the cell culture stimulation experiments. Agar plates were obtained by adding 1.5% of agar to the above described respective medium.

1.7) Motility

Motility measurements were performed with corpus circular muscle preparations from Dunkin Hardley guinea pigs (Sulzfeld and Harlan Winkelmann GmbH, Borchen, Germany). Contractile force of the muscle was measured using force transducer in organ bath using LabChart 5 software (ADInstruments, Spechbach, Germany). Briefly, stomach muscle tissue was dissected from mucosa layer in continuously perfused ice-cold preparation Krebs solution (pH 7.4) ($MgCl_2 \times 6H_2O$ 1.2 mM, $CaCl_2 \times 2H_2O$ 2.5 mM, $NaH_2PO_4$ 1.2 mM, NaCl 117 mM, $NaHCO_3$ 25 mM, $C_6H_{12}O_6$ 11 mM, KCl 4.7 mM). A 1.5 cm$^2$ piece of corpus circular muscle was cut out and mounted from both ends with polyamide thread between two electrodes into organ bath in 20 mL experimental Krebs solution (identical to preparation Krebs except for $NaHCO_3$ 20 mM) at 37° C. and aerated continuously with Carbogen (95% $O_2$ and 5% $CO_2$). After an equilibration period of 45 min muscle preparations were stimulated by electrical field stimulation (EFS) to test vitality. The change in contractile force during EFS as well experimental treatment was measured by the force transducer. The time lapse between any treatments was always 20 min.

1.8) Ussing Chamber

The ion movement across intestinal epithelia was measured with Ussing chamber technique (Easy mount chambers, Physiologic instruments, San Diego, USA) and LabChart 5 software (ADInstruments, Spechbach, Germany). Briefly segments, of the distal colon of Dunkin Hardley guinea pigs (Sulzfeld and Harlan Winkelmann GmbH, Borchen, Germany) were dissected, the muscle layers removed and mucosa/submucosa preparations were mounted into slider with a recording area 0.5 cm$^2$. Apical and basolateral sides were bathed separately in 5 mL Krebs solution. During experimental procedures, the bath was maintained at 37° C. and aerated continuously with Carbogen (95% $O_2$ and 5% $CO_2$). After an equilibration period of 45 min tissue was electrically stimulated (Parameters: stimulus strength 6V, duration 10 sec, frequency 10 Hz, single pulse duration 0.5 ms) to assess tissue vitality. For assessment of active ion transport spontaneous occurring transepithelial voltage ($V_{TE}$) formed by passive ion transport across the tissue was set to 0 mV by applying short circuit current ($I_{SC}$). When the active chloride ion secretion is induced an increase in $I_{SC}$ is observed necessary to keep $V_{TE}$ at 0 mV. The change in $I_{SC}$ is equivalent to the current generated by the anions secretion or cation absorption. Transepithelial resistance (TER=$V_{TE}/I_{SC} \times 1000/2$) of tissue was measured at the beginning and at the end of each experiment to assess the tissue integrity.

1.9) Statistical Analysis

Data are expressed as mean values±standard deviation (SD). All statistical computations were performed using Statistical programming platform R comparing treatment vs. corresponding control group were analyzed using unpaired t-tests. Data comparing several treatments vs. corresponding control group were analyzed using One-Way ANOVA followed by an appropriate multiple comparison procedure. If data was not normally distributed or comprised discontinuous data, non-parametrical tests (Mann-Whitney/Rank sum test, ANOVA on ranks) were used. Differences were considered significant if p-values were <0.05 (*) or <0.01 (**). Principal component analysis (PCA) is described in Pearson, K.; On Lines and Planes of Closest Fit to Systems of Points in Space, Philosophical Magazine (1901), 2 (11), 559-572 and Theodoridis, G., Gika, H. G., Wilson, I. D.; LC-MS-based methodology for global metabolite profiling in metabonomics/metabolomics, TrAC Trends in Analytical Chemistry (2008), 27 (3), 251-260.

2.) Results 2.1) LC-MS/MS Analysis of Metabolites in Extracts from Sourdough, Sourdough Bread and Analog Bread To compare the effect of fermentation on sourdough and sourdough bread water soluble extracts (<10 kDa, triplicates) of raw sourdough, sourdough bread and analog bread prepared from three different batches were subjected to LC-MS/MS analysis. The concentration of metabolites in extracts was determined by comparison to the standard solution with known concentration of metabolites.

Figure 1B:
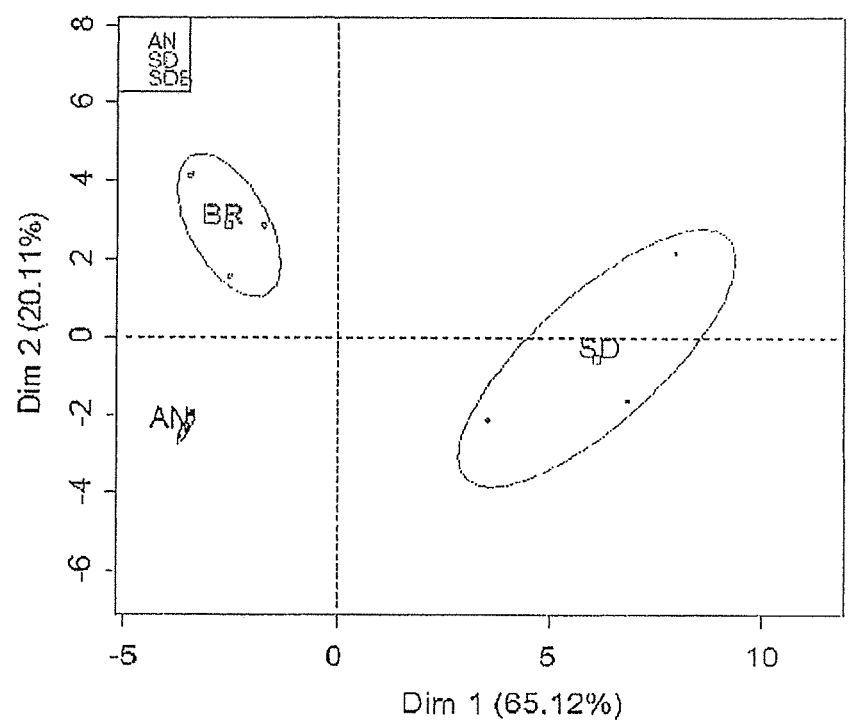

Principal component analysis (PCA) demonstrated significant differences in metabolites isolated from sourdough, sourdough bread and analog bread (FIG. 1). Raw sourdough has significantly higher amounts of free amino acids reflecting proteolitic acitivity of endogenous flour enzymes as well as lactic acid bacteria proteases. Before baking fresh unfermented flour is added to the sourdough explaining why there are no differences in the free amino acid content between analog and sourdough bread. Acetylcholine is a metabolite that is consistently present in sourdough and sourdough bread but not in analog bread (Table 1). Fermentation by sourdough bacteria is the only difference between sourdough bread and analog bread, suggesting acetylcholine is produced by microorganisms present in sourdough.

TABLE 1

Sourdough and sourdough bread contain high amounts of acetylcholine of with 38.6 mg/kg in dry bread. Concentration was determined using LC-MS/MS by comparing the peak area to the area of solutions with standard concentrations of acetylcholine.

| Water extracts | ACH concentration in water extracts | ACH concentration in bread or sourdough, dry mass |
|---|---|---|
| Sourdough, 10 kDa | 1819 ± 717 µM | 26.5 ± 10.4 mg/kg |
| Sourdough bread, 10 kDa | 2644 ± 273 µM | 38.6 ± 4.03 mg/kg |
| Analog bread, 10 kDa | 44.5 ± 1.0 µM | 0.64 ± 0.03 mg/kg |

2.2) Sourdough-Derived Acetylcholine Triggers Muscle Contraction In Vitro

Figure 2:
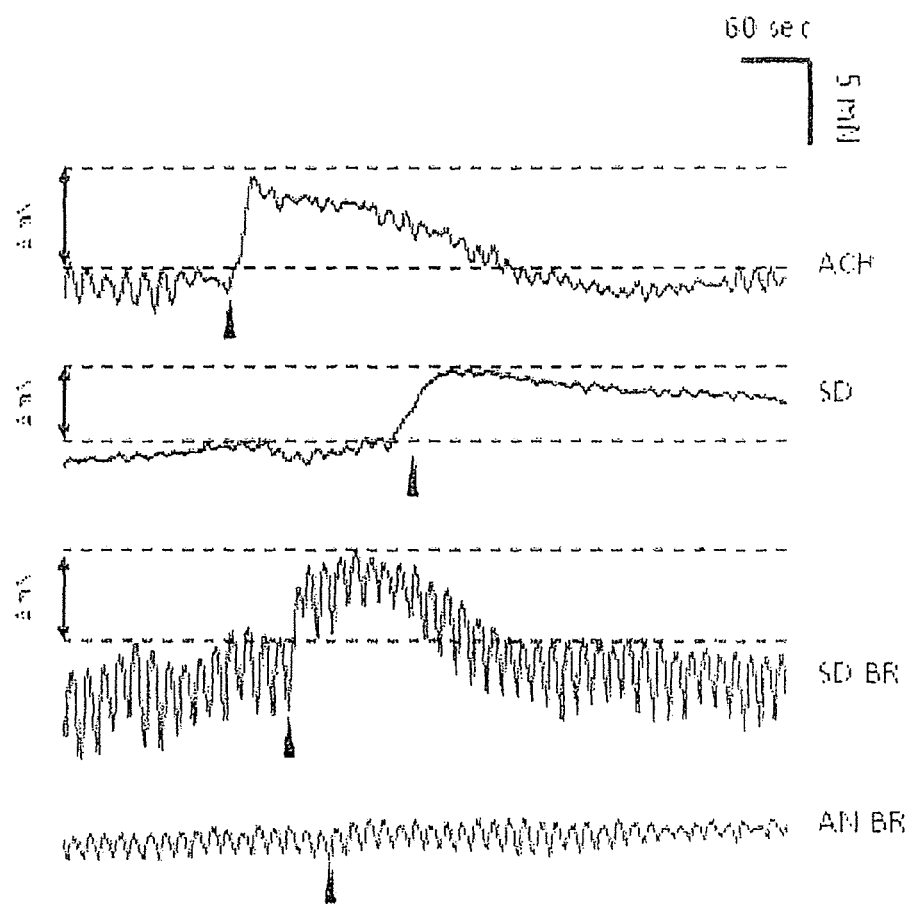
FIGS. 2A-2B: Sourdough extracts effectively stimulate stomach muscle motility by acting directly on muscarinic acetylcholine receptor (mACHR). A: Muscle tone change induced by either acetylcholine (ACH) (2.5 µM) or extracts of sourdough (SD), sourdough bread (BR) or analog bread (AN BR) at 0.02%. Increase in tone was immediately observed upon addition of the stimulants (arrow sign) except for extract of analog bread. B: Median (n>4) change of muscle tone upon differential treatments. The pro-kinetic effect of acetylcholine (ACH) and extracts of sourdough (SD), sourdough bread (BR) or analog bread (AN BR) is completely abolished by mACHR specific antagonist atropine. This indicates that acetylcholine in extracts directly acts on mACHR.

Acetylcholine (ACH) is a neurotransmitter that is responsible for the activation of motility in the gastro-intestinal tract by stimulating either muscarinic (mACHR) or nicotinic ACH receptors (nACHR) on the muscle cells. To determine if the sourdough-derived acetylcholine mimicks this activity, isolated corpus muscle of guinea pig was stimulated with extracts of sourdough, sourdough bread and analog bread and the contraction stimulation was measured. Both sourdough and sourdough extracts but not analog bread extract induced muscle contractions similar to acetylcholine at equivalent concentration (FIG. 2). Atropine, mACHR-specific antagonist, was used to determine whether extracts stimulate contraction by activating muscarinic or nicotinic ACHR. Pre-treatment of muscle strips with atropine completely abrogated stimulation by ACH as well as by sourdough and sourdough bread extracts indicating that sourdough-derived acetylcholine is acting via mACHR.

Figure 3:
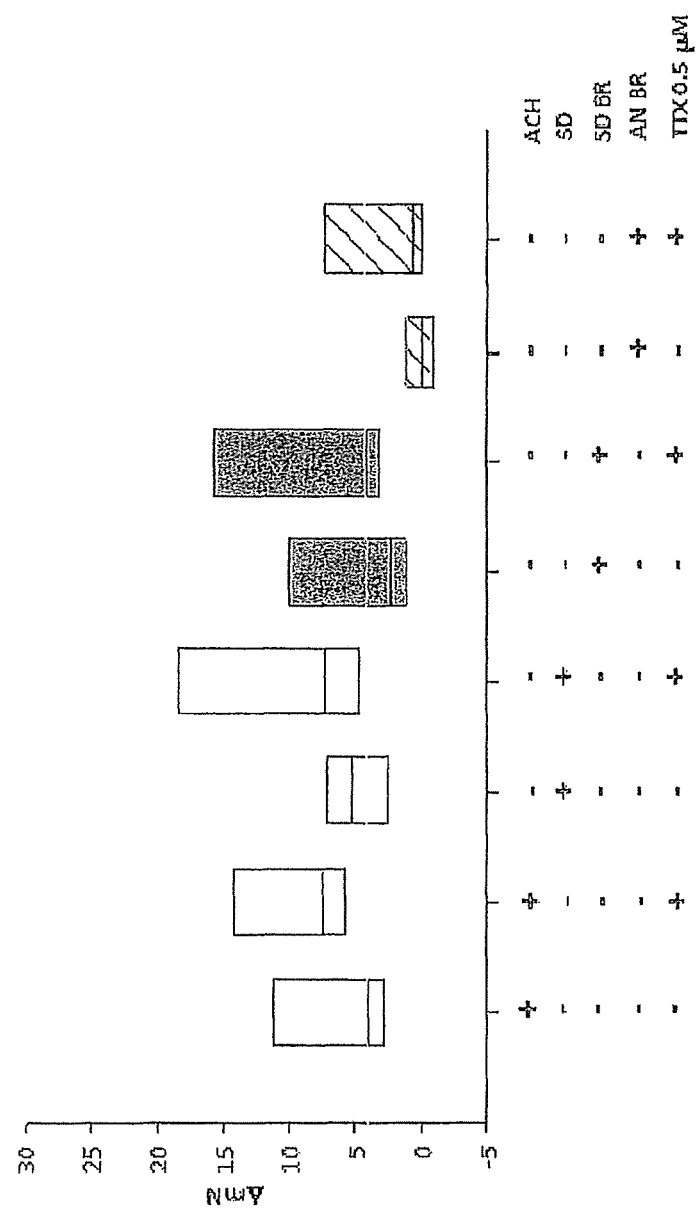
FIG. 3: Tetrodotoxin (TTX) has no significant effect on the stimulation of muscle contraction by sourdough (SD)-derived acetylcholine (ACH). The figure shows the muscle tone change stimulated by either acetylcholine (2.5 µM) or 0.02% extracts of sourdough (SD), sourdough bread (BR) or analog bread (AN BR), and the effect of TTX pre-treatment. TTX did not exhibit significant effect on the muscle contraction induced by sourdough ACH suggesting stimulation is induced by direct action on muscle mACHR without neuronal mediation.

Furthermore to clarify whether sourdough-derived ACH acts through the activation of neurons that consequently stimulate muscle cells, muscle preparations were pre-treated with tetrodotoxin (TTX). TTX blocks action potential generated by neurons that abrogates downstream signalling. TTX pre-treatment had no significant effect on muscle contraction induced by acetylcholine and extracts suggesting that both directly activate mACHR on muscle cells (FIG. 3). Motility is one of the crucial functions of the GI tract. Agonists and antagonists of serotonin (5-hydroxytryptamine) receptors are a common treatment option for modulating motility and consequently bowel movements of IBS patients (Camilleri, M. and V. Andresen, Current and novel therapeutic options for irritable bowel syndrome management. Dig Liver Dis, 2009. 41(12): p. 854-62). These observations show that external application of ACH at local sites could also be utilised to modulate ENS-mediated motility.

Figure 4:
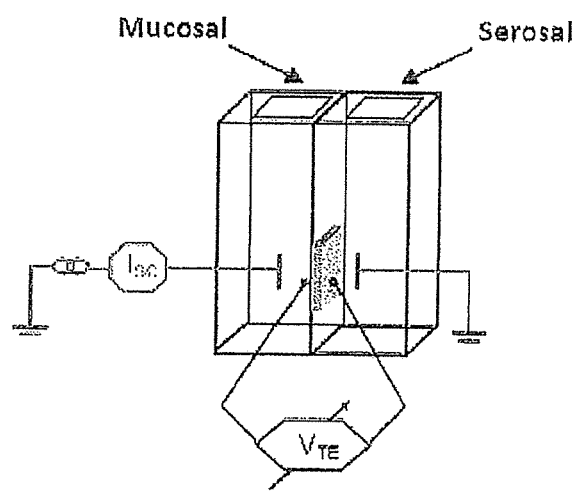
FIGS. 4A-4C: Sourdough and sourdough bread extracts stimulate chloride ions secretion when applied from either serosal or mucosal side of intestinal mucosa. A: Ussing chamber set-up with mucosa piece separating the two chambers. The lower set of electrodes measure transepithelial voltage ($V_{TE}$) and the lateral set—the short circuit current ($I_{SC}$). The secretion is measured estimated by the change in $I_{SC}$ necessary to maintain $V_{TE}$ at 0 mV. B: Representative $I_{SC}$ traces stimulated by acetylcholine (ACH), sourdough (SD), sourdough bread (SD BR) or analog bread (AN BR) extracts. Area under the curve is calculated using an integral ($µA*s/cm^2$) where blue shows response to extracts and red-striped shows response to electric field stimulation (EFS). Figure C shows median (n>4) value of change in $I_{SC}$ upon treatment on either mucosal side (MUC) or serosal side (SER) of guinea pig colonic mucosa. Acetylcholine (ACH) and sourdough (SD) as well as sourdough bread (SD BR) extracts clearly stimulate secretion when applied to either side of mucosa while analog brad extract has no effect. Showing that acetylcholine in sourdough and sourdough bread is responsible for the stimulation.
Figure 4B:
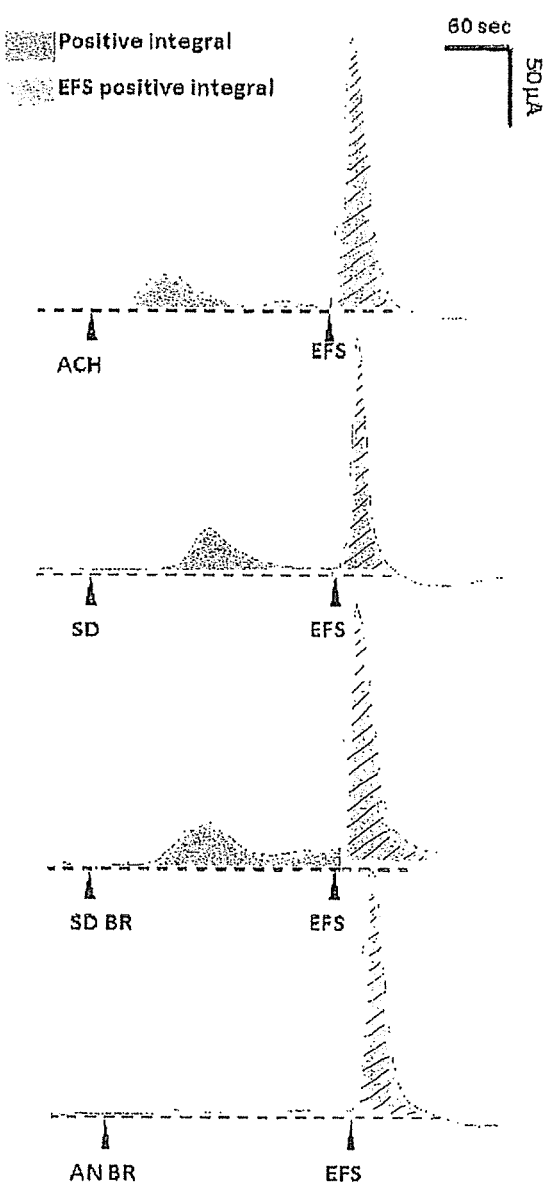

2.3) Sourdough-Derived Acetylcholine Stimulates Secretion by the Intestinal Mucosa from the Luminal Side Acetylcholine (ACH), released by the enteric neurons to the serosal side of the intestinal wall, stimulates secretion of chloride ions by the mucosa subsequently driving the passive transport of water into the lumen. This effect is transient due to rapid degradation of acetylcholine by acetylcholine esterase. The effect of sourdough-derived ACH on the intestinal secretory function was tested in guinea pig colon. Extracts of sourdough, sourdough bread, analog bread as well as (pure) ACH were applied on either luminal (mucosal) or serosal side of intestinal mucosa/submucosa preparations from guinea pig distal colon. The experiment was performed in Ussing chamber and the change in short-circuit current ($I_{SC}$) was measured. In this system, passive flow of ions across a tissue or epithelial cell layer is eliminated by balancing electrical, osmotic, hydrostatic and chemical gradients across the preparation, such that only active ion transport is measured. In the Ussing chamber, electrodes are placed close to each side of the tissue to allow detection of the spontaneous potential difference (PD) across the epithelium, generated as a consequence of active ion transport (Hirota, C. L. and McKay D. M., Cholinergic regulation of epithelial ion transport in the mammalian intestine, Br. J. Pharmacol., 2006, 149(5):p. 463-79). Surprisingly an increase in $I_{SC}$ could be observed when the preparations were stimulated from both mucosal and serosal side by ACH as well as ACH-containing extracts (analog bread extract had no effect) (FIG. 4), showing that acetylcholine in sourdough and sourdough bread is suitable for the stimulation.

Figure 5A:
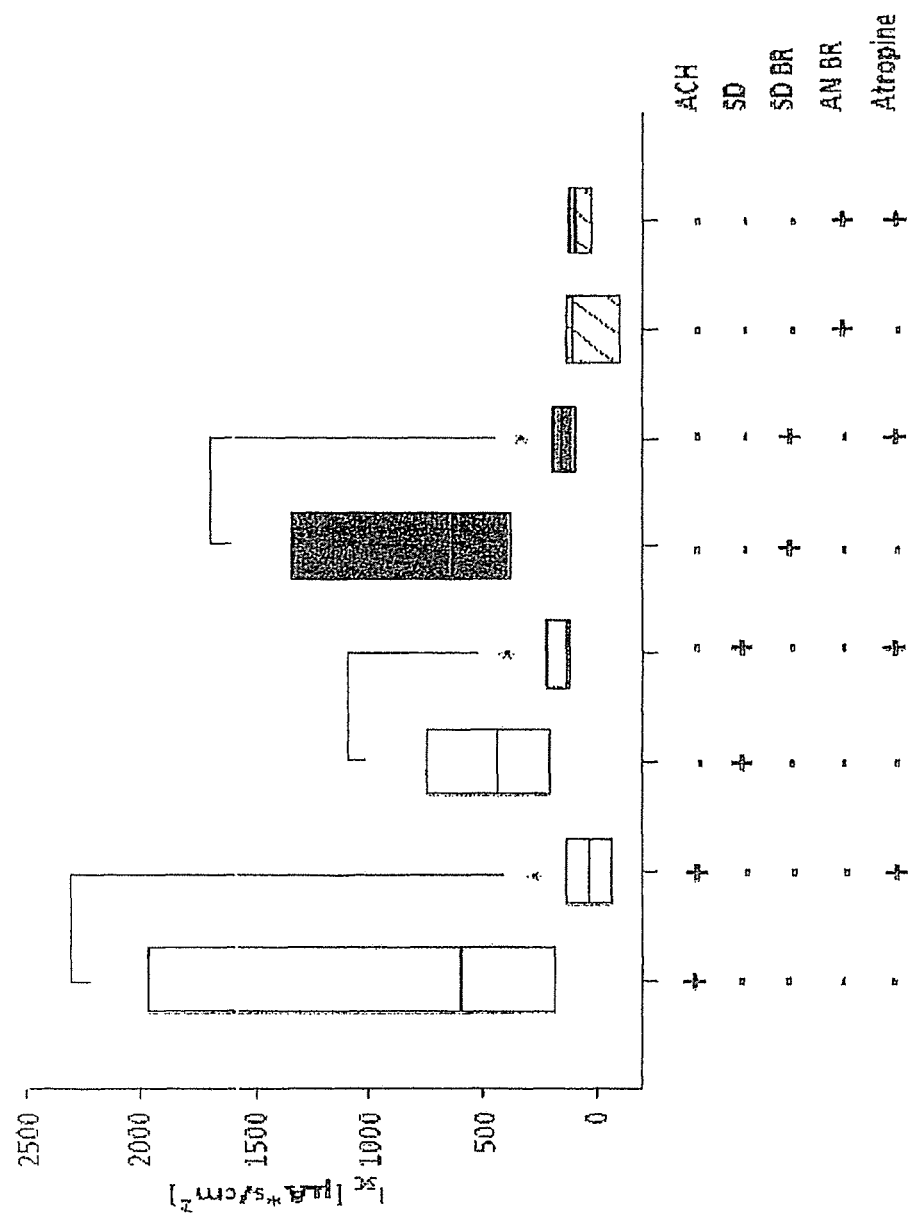
FIGS. 5A-5B: Atropine completely abrogates chloride ion secretion stimulated with sourdough (SD) and sourdough bread (SD BR) extracts. Shown is the mean (n>4) value of change in short circuit current ($I_{SC}$) over time upon acetylcholine (ACH) (10 µM) and extract (0.1%) application on either mucosal side (A) or serosal side (B) of guinea pig colonic mucosa with and without atropine pretreatment (1 µM). Atropine completely abrogated secretion stimulation suggesting the role of mACHR in the secretory effect of sourdough extracts.
Figure 5B:
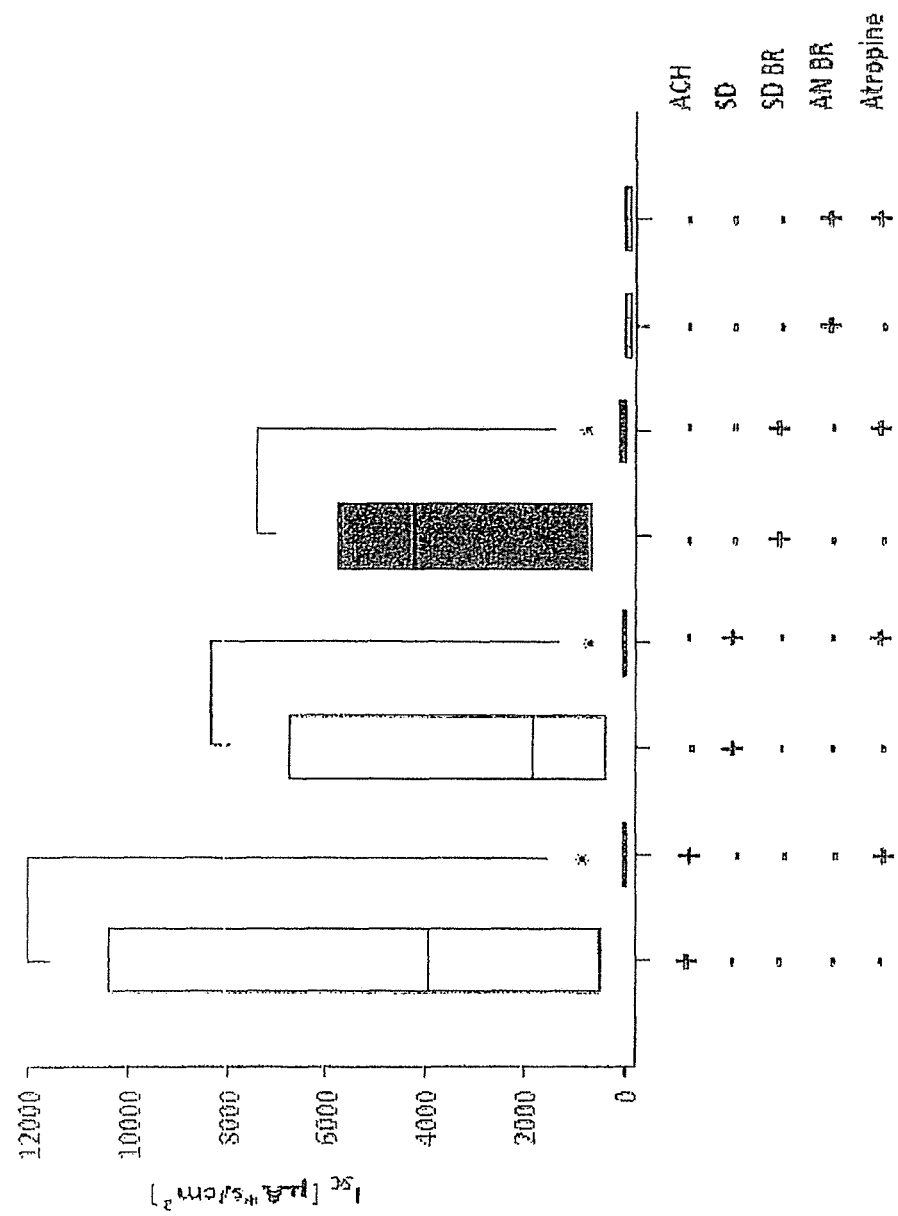

The tissue was pre-treated with atropine and the effect of extracts on secretion measured again (FIG. 5). Atropine completely abolished the response corroborating the role of mACHR in the pro-secretory effect of sourdough extracts.

Figure 6:
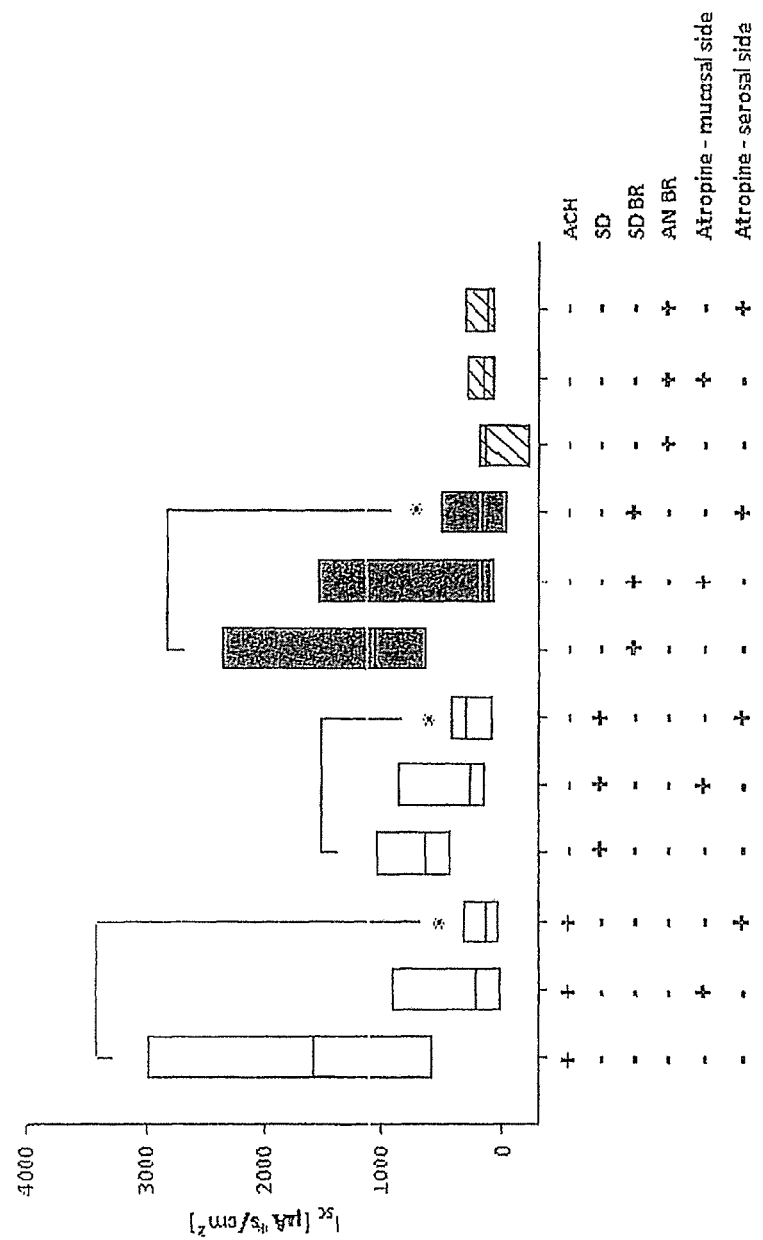
FIG. 6: Atropine completely abrogates secretion stimulation by ACH and extracts of sourdough (SD), sourdough bread (BR) or analog bread (AN BR) when applied serosally but not mucosally. Shown is the mean (n>4) value of change in short circuit current ($I_{SC}$) over time subsequent to ACH and extract treatment on the mucosal side with and without atropine pre-treatment (1 µM). Atropine was added on either serosal or mucosal side. Atropine completely abrogated secretion when applied on serosal but not mucosal side.

Earlier research provides evidence of the expression of ACHR in intestinal epithelial cells on the basolateral side but not on the apical side of the cell layer (Hirota, C. L. and McKay D. M., Cholinergic regulation of epithelial ion transport in the mammalian intestine, Br. J. Pharmacol., 2006, 149(5):p. 463-79). Therefore it is highly probable that ACH applied from apical side crosses the cell layer and stimulates the receptors on the basolateral side. This hypothesis was verified by the fact that when ACH is applied apically, i.e. on the mucosal or luminal side, the secretory effect was significantly inhibited when atropine was applied to the serosal but not to the mucosal side (FIG. 6). Atropine applied on the serosal side blocked all mACHR on basolateral side abrogating ACH activity. However, when atropine is applied on the mucosal side this results into smaller amounts reaching basolateral side and thus only partially inhibiting ACH activity. The observation that atropine can cross epithelial layer and block basolateral mACHR was confirmed by the fact that when ACH was applied serosally and atropine mucosally secretion was inhibited (data not shown).

These observations show that external application of ACH at local sites could also be utilised to modulate ENS-mediated fluid secretion. This is especially important, since fluid secretion into the intestine is hypothesized to provide the ideal environment for enzymatic digestion and to facilitate the passage of stool through the intestinal tract. Furthermore recent studies suggest that acute and locally targeted water secretion serves as a protective measure against epithelial damage at points of particular mechanical stress (Barrett, K. E. and S. J. Keely, Chloride secretion by the intestinal epithelium: molecular basis and regulatory aspects. Annu Rev Physiol, 2000. 62: p. 535-72 and Sidhu, M. and H. J. Cooke, Role for 5-HT and ACh in submucosal reflexes mediating colonic secretion. Am J Physiol, 1995. 269(3 Pt 1): p. G346-51).

2.4) LC-MS/MS Analysis Revealed Presence of Acetylcholine in Growth Media of Sourdough Lactic Acid Bacteria Seven strains of *L. sanfranciscensis* (DSM 23090-DSM 23201) and *L. rossiae* (DSM 26024) isolated from sourdough, *L. plantarum* FUA 3038 and *L. brevis* 3113 isolated from another sourdoughs, and *L. paracasei* (VSL #3) were grown for 24 hours in MRS media. The growth media was collected, filtered and analyzed using LC-MS/MS.

Figure 7:
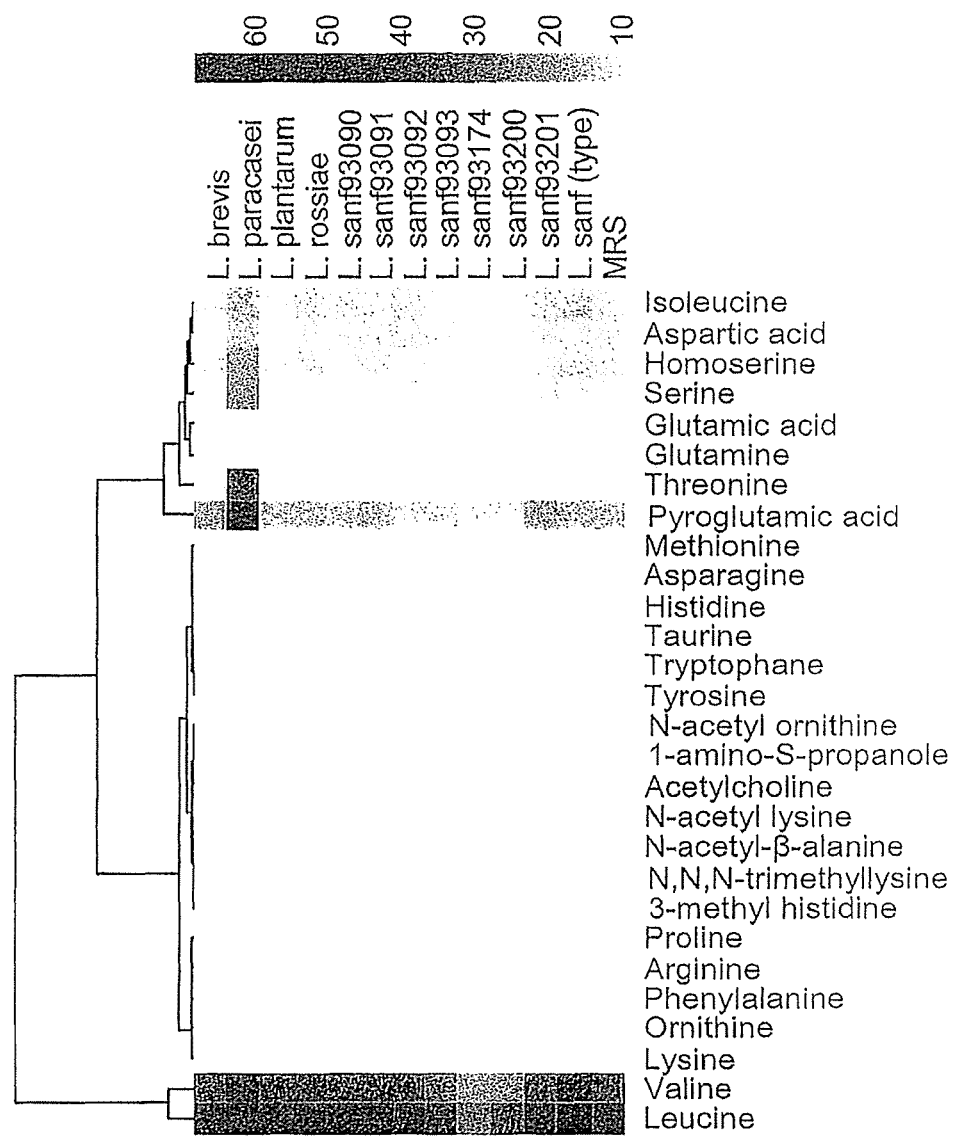
FIGS. 7A-7C: Metabolic profile of sourdough lactic acid bacteria. A: Heatmap of absolute metabolite values in MRS broth after 24 hour lactic acid bacteria inoculation (mean of three experiments). B: PCA plot of metabolites indicates sharp distinction between tested sourdough bacteria and L. paracasei (LC). C: Acetylcholine (ACH) plays the strongest role in the separation observed in PCA plot since L. paracasei does not produce any Acetylcholine.
Figure 7B:
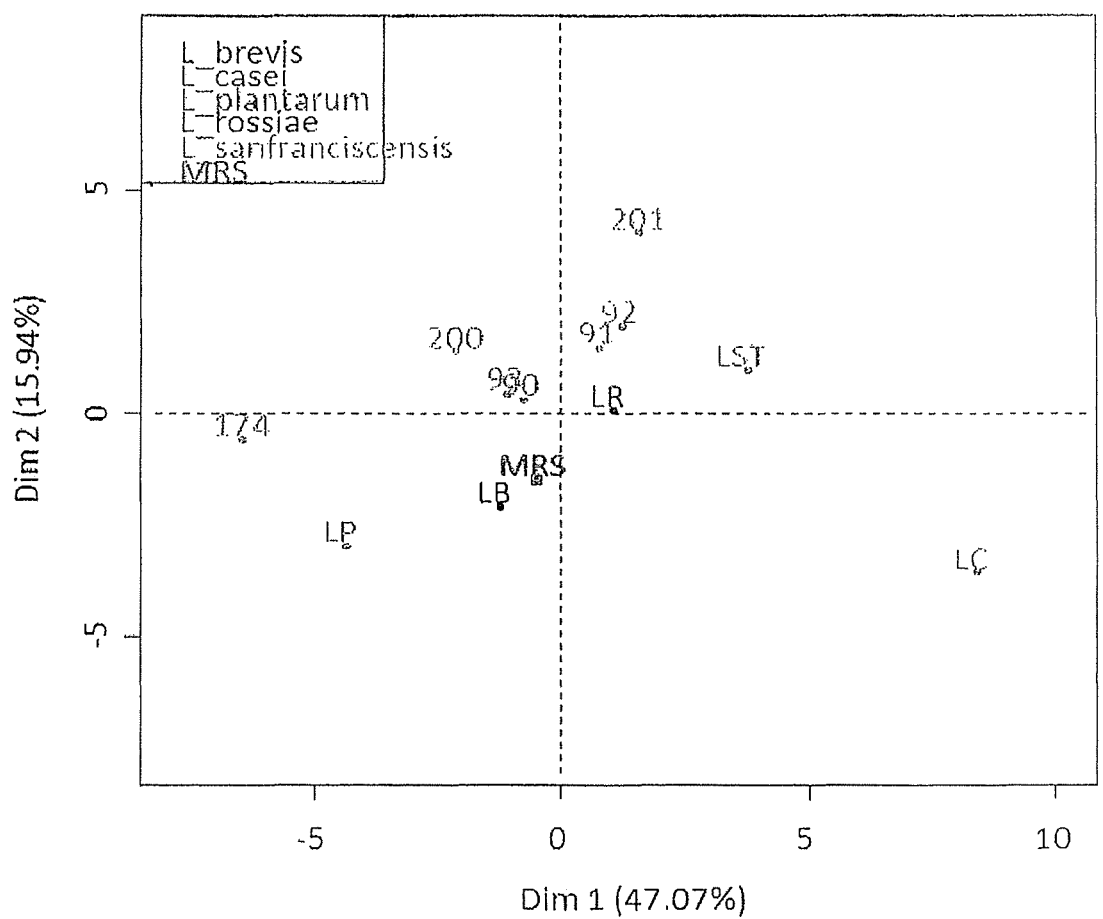
Figure 7C:
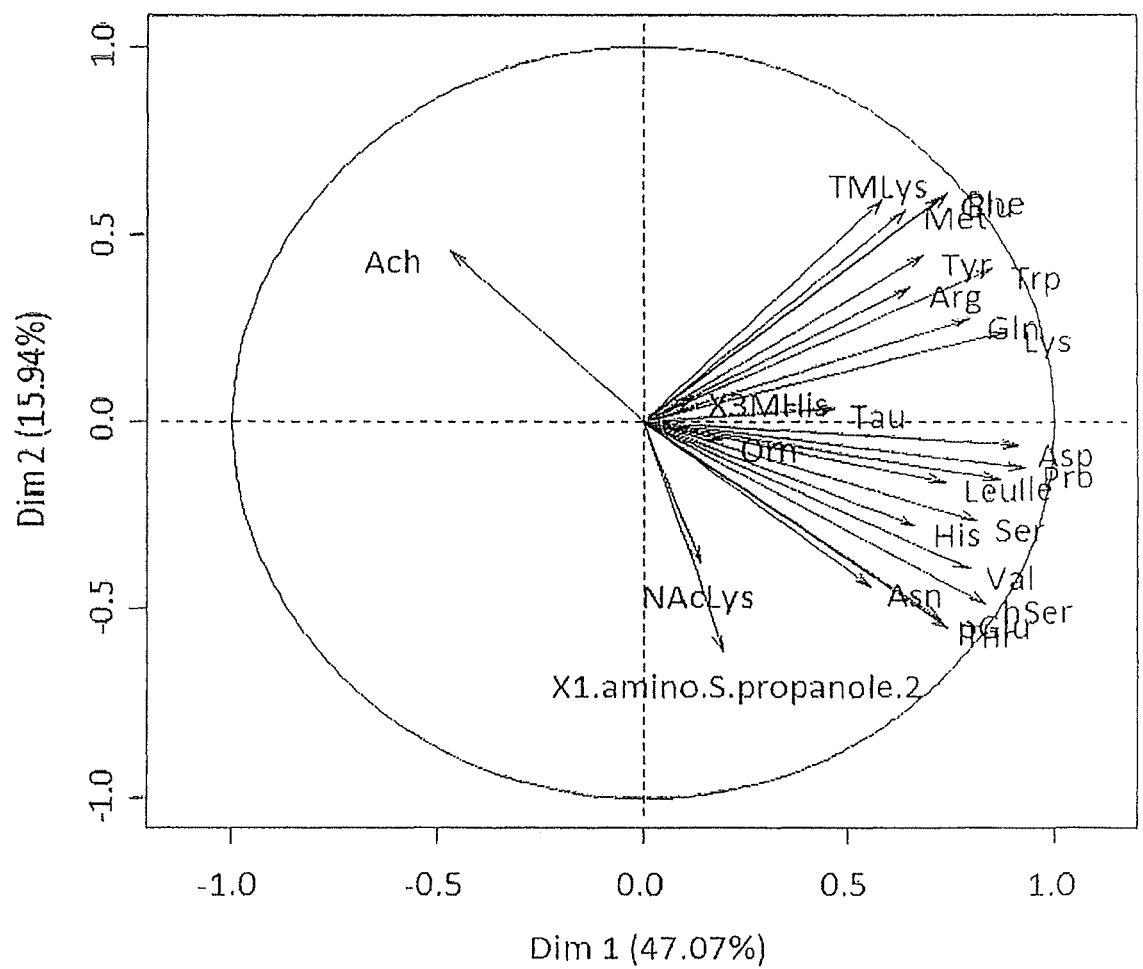
Figure 8A:
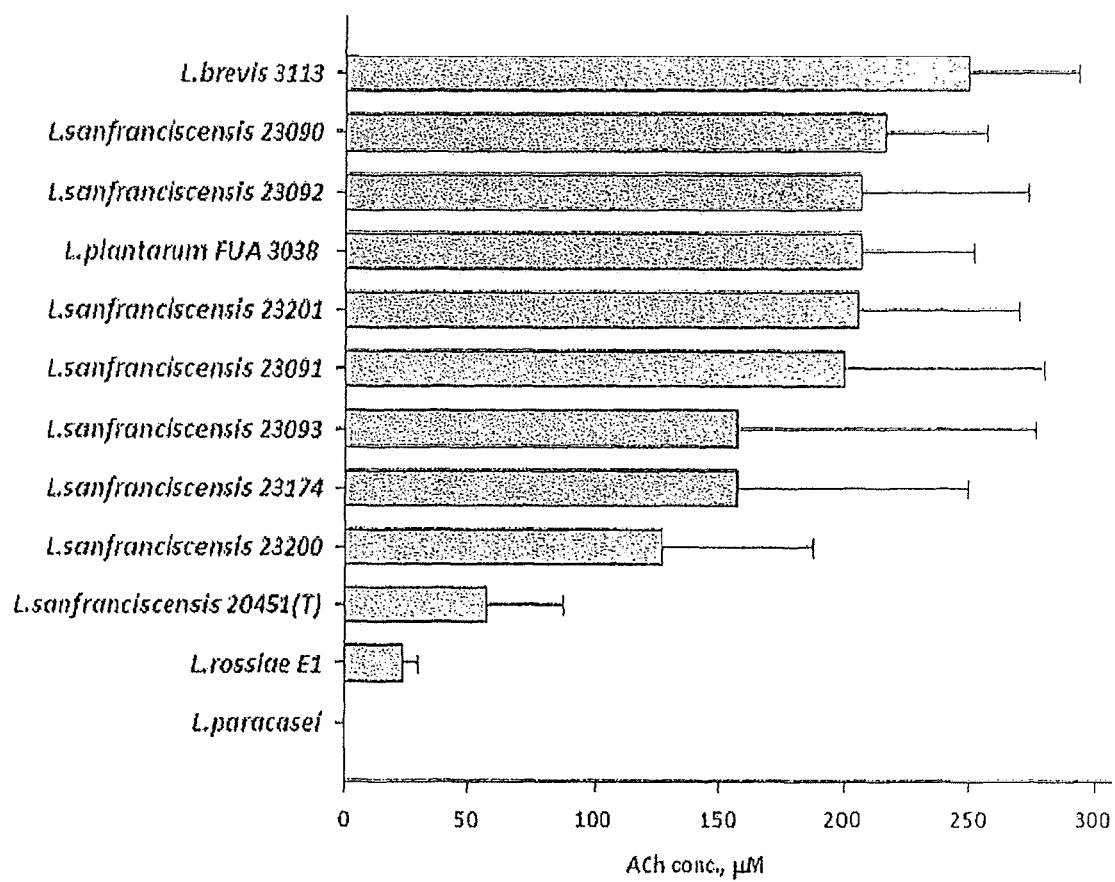
FIGS. 8A-8B: Acetylcholine concentration in MRS media upon 24 hours of incubation with lactic acid bacteria. A: Acetylcholine concentration in MRS broth upon 24 hour inoculation with $0.25 \times 10^7$ of bacteria/mL. B: Acetylcholine (ACH) concentration adjusted to $10^6$/mL bacteria count in MRS. Concentration was determined using LC-MS/MS by comparing the peak area to the area of solutions with known concentration of acetylcholine.
Figure 8B:
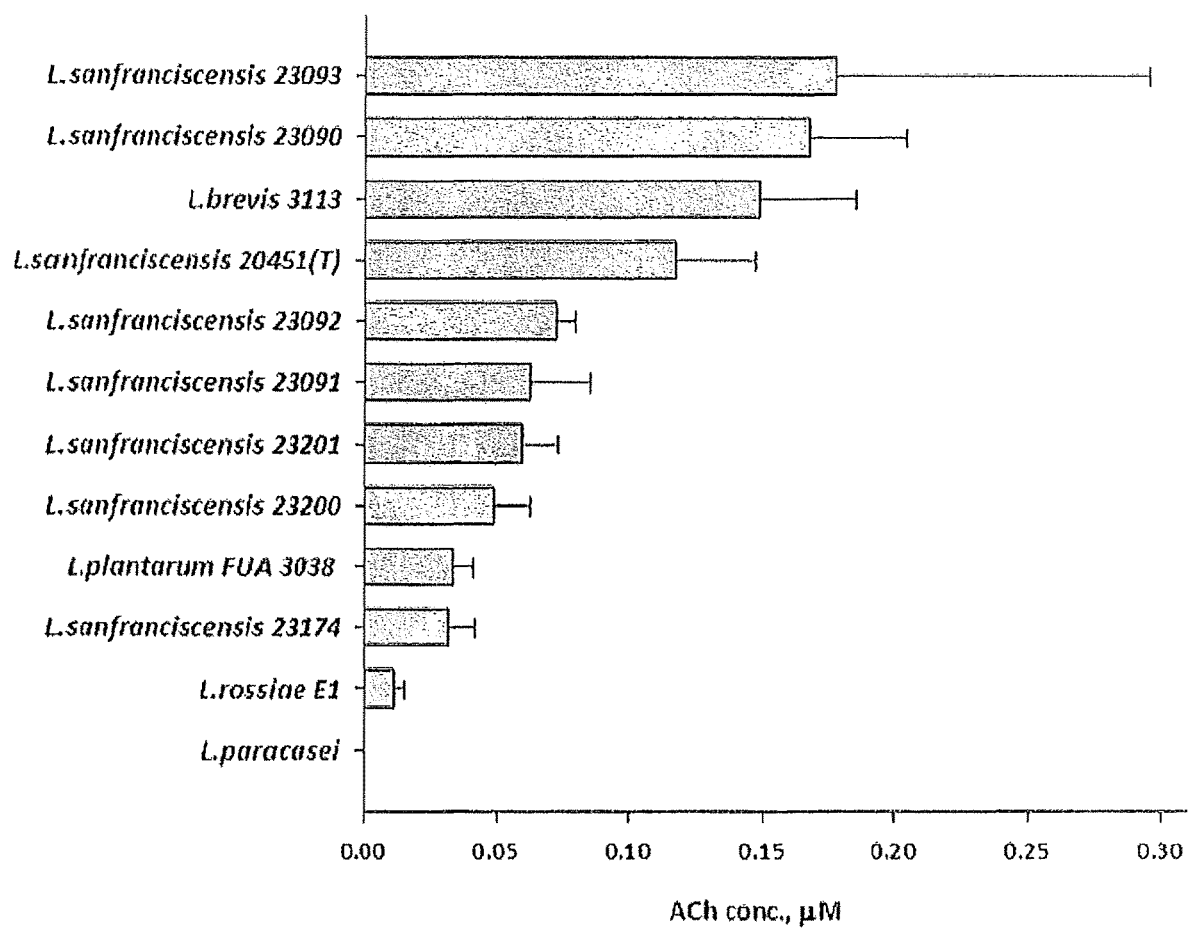

PCA analysis shows significant difference in the metabolites profiles of all sourdough isolated bacteria compared to *L. paracasei*. The separation is due in major part to the impact of acetylcholine present in sourdough bacteria growth media but not in *L. paracasei* media (FIG. 7). The highest ACH producer over 24 hours is *L. brevis* 3113, which additionally has the highest growth rate (FIG. 8A). However when the concentration is adjusted to a bacterial number, e.g. $10^6$/ml, in the broth, the most ACH per bacterial cell is produced by *L. sanfranciscensis* strains DSM 23090 and DSM 23093 (FIG. 8B).

Figure 9:
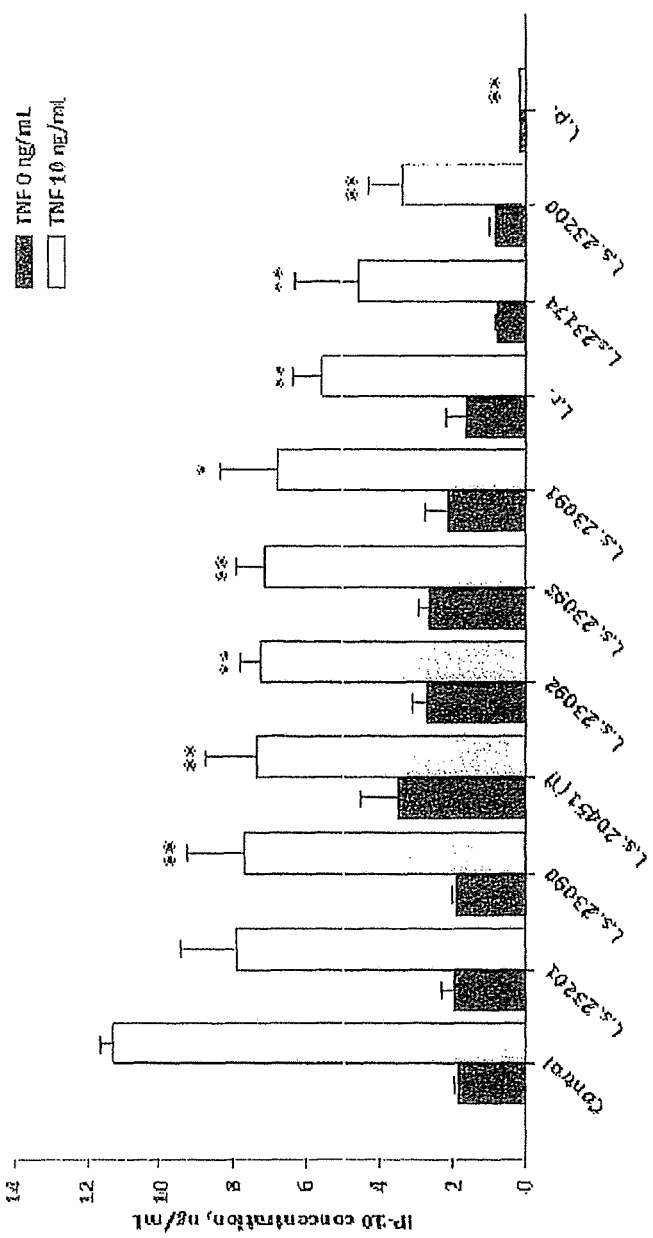
FIG. 9: Concentrated conditioned media of sourdough lactic acid bacteria significantly inhibits the secretion of interferon inducible protein 10 (IP-10) by tumor necrosis factor (TNF)-activated intestinal epithelial cells (IEC). The concentration of IP-10 in the culture media of Mode-k cells as measured by ELISA is shown. The cells were incubated for 24 hours with concentrated conditioned media (cCM) (black bar) and cCM plus 10 ng/mL TNF (grey bar). L. paracasei (L.p.) expresses Lactocepin PrtP that is capable of efficiently degrading IP-10 and as expected has the highest inhibitory activity. The cCM of sourdough lactic acid bacteria significantly inhibit IP-10 secretion but to a lesser extent. L. sanfranciscensis strains DSM 23174 and DSM 23200 are the most efficient in inhibiting IP-10 secretion next to L. paracasei.
Figure 10:
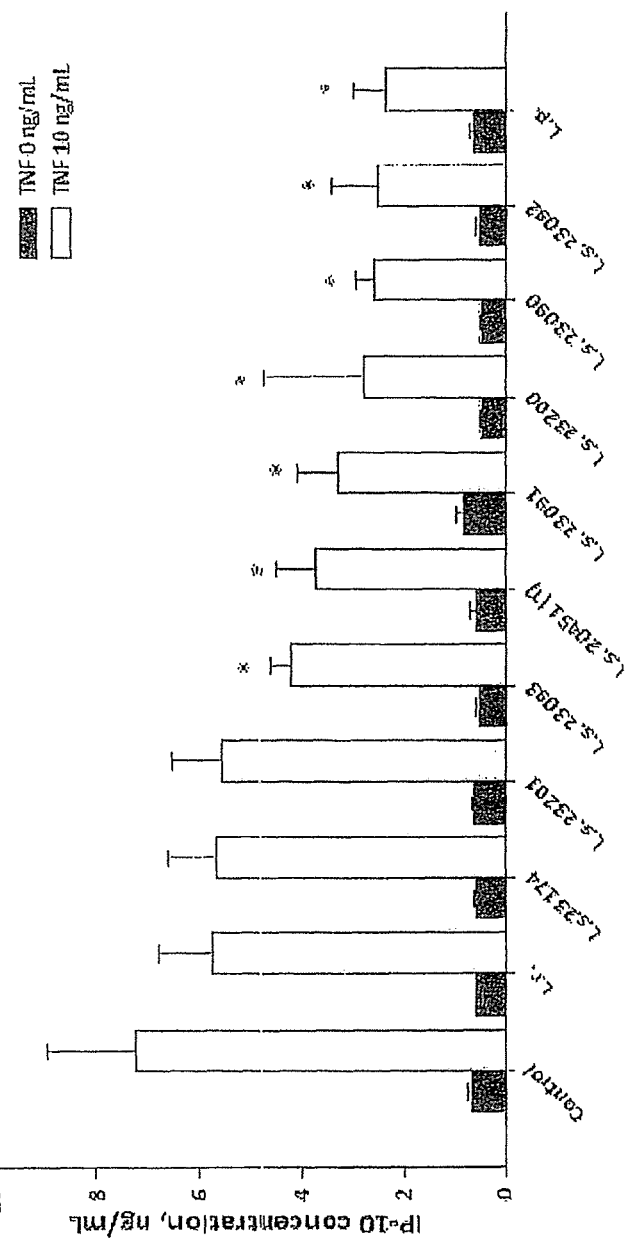
FIG. 10: Formaldehyde-fixed sourdough lactic acid bacteria significantly inhibit the secretion of interferon inducible protein (IP-10) by TNF-activated intestinal epithelial cells. The concentration of IP-10 in the culture media of Mode-k cells as measured by ELISA is shown. The cells where incubated for 24 hours with 20 MOI of fixed lactic acid bacteria (black bar) and 20 MOI of fixed lactic acid bacteria plus 10 ng/mL tumor necrosis factor (TNF) (grey bar). Fixed L. paracasei (L.p.) has, similar to fixed L. sanfranciscensis strains DSM 23090 and DSM 23092, the highest inhibitory activity on the IP-10 secretion by TNF-activated intestinal epithelial cells (grey bar) as compared to TNF-activated control.

2.5) Sourdough Lactic Acid Bacteria Inhibit Secretion of Chemokine IP-10 by TNF-Activated Intestinal Epithelial Cells Lactocepin PrtP, a serine protease expressed in *L. paracasei* (VSL #3), selectively degrades pro-inflammatory chemokine interferone inducible protein 10 (IP-10). To investigate if PrtP is also present in the Lactobacilli of the present invention, the total bacterial DNA was isolated from eight sourdough strains: *L. sanfranciscensis* (DSM 23090, DSM 23091, DSM 23092, DSM 23093, DSM 23174, DSM 23200, DSM 23201) and *L. rossiae* (DSM 26024) as well as *L. paracasei* as positive control. DNA was amplified using Lactocepin PrtP specific primers and visualized on agarose gel. No detectable amounts of lactocepin PrtP gene were present in sourdough-isolated lactic acid bacteria. The eight sourdough lactic acid bacteria strains and *L. paracasei* were tested for their effects on the secretion of pro-inflammatory chemokine IP-10 by unstimulated and TNF-activated Mode-K cells. Interestingly, both conditioned media (FIG. 9) and fixed lactic acid bacteria (FIG. 10) demonstrated IP-10 inhibitory activity despite the fact that no Lactocepin PrtP gene was detected. This suggests that there are both secreted and cell surface-bound factors produced by sourdough lactic acid bacteria suitable to inhibit secretion of pro-inflammatory chemokine IP-10. This result provide a basis for potential treatment of IBD and relief of their symptoms, since IP-10 has been implicated in re-enforcing intestinal inflammation in IBD patients.

The invention claimed is:

1. A method of treating and/or reducing the risk of intestinal diseases comprising administering a living acetylcholine-producing microorganism to a patient in need thereof, wherein the intestinal disease is a disorder associated with impaired intestinal motility and secretion or an inflammatory bowel disease and wherein said microorganism is selected from the group consisting of *Lactobacillus sanfranciscensis* and *Lactobacillus rossiae*, wherein said *Lactobacillus rossiae* is DSM 26024 and said *Lactobacillus sanfranciscensis* is selected from the group consisting of DSM 23090, DSM 23091, DSM 23200, DSM 23092, DSM 23093, DSM 23201, DSM 23121 and DSM 23174.

2. The method according to claim 1, wherein said living acetylcholine-producing microorganism is administered in an amount sufficient for maintaining a healthy gut flora, promoting a healthy gut flora, reducing the toxic effects of the digestive process, stimulating the digestive system and/or improving intestinal control.

3. The method according to claim 1, wherein the intestinal disease is a functional bowel disorder.

4. The method according to claim 1, wherein the intestinal disease is a functional intestinal disorder and/or a disorder associated with secretions of the intestinal wall controlled by the enteric nervous system.

5. The method according to claim 1, wherein the intestinal disease is functional constipation, functional diarrhea and/or irritable bowel syndrome (IBS).

6. The method according to claim 1, wherein the intestinal disease is constipation predominant IBS, alternating IBS or diarrhea predominant IBS.

7. The method according to claim 3, wherein the functional bowel disorder is a chronic or semi-chronic gastrointestinal disorder which is associated with bowel pain, disturbed bowel function and/or social disruption.

8. The method according to claim 1, wherein the intestinal disease is ulcerative colitis and/or Crohn's disease.

9. The method according to claim 1, wherein the microorganism produces >20 mg acetylcholine/kg weight of the medium when culturing with MRS-broth and adjusting the acetylcholine concentration to a $10^6$/ml bacteria count.

10. The method according to claim 1, wherein the microorganism is a DSM 23090 or DSM 23093 strain.

11. The method according to claim 1, wherein said living acetylcholine-producing microorganism is in a pharmaceutical dosage form, a functional food or in a functional beverage.

12. The method according to claim 11, wherein the functional food is sourdough bread.

13. The method according to claim 1, further comprising administering at least one additional bacterium for maintaining and/or restoring a favorable gut flora.

14. The method according to claim 1, further comprising administering at least one additional medicament for the treatment of intestinal diseases.

15. The method according to claim 1, wherein the inflammatory bowel disease is chronic.

\* \* \* \* \*